US012447326B2

(12) United States Patent
Dixson et al.

(10) Patent No.: US 12,447,326 B2
(45) Date of Patent: Oct. 21, 2025

(54) MODULAR MEDICAL DEVICES AND METHODS OF USING THE SAME

(71) Applicant: Boston Scientific Scimed, Inc., Maple Grove, MN (US)

(72) Inventors: Erin Dixson, Westborough, MA (US); John B. Golden, Norton, MA (US); Michael Jacobs, Franconia, NH (US); Richard Kim, Chestnut Hill, MA (US); Alyanna Tenorio, Quincy, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 622 days.

(21) Appl. No.: 17/863,199

(22) Filed: Jul. 12, 2022

(65) Prior Publication Data

US 2023/0023094 A1 Jan. 26, 2023

Related U.S. Application Data

(60) Provisional application No. 63/221,426, filed on Jul. 13, 2021.

(51) Int. Cl.

*A61B 1/00* (2006.01)
*A61M 39/10* (2006.01)
*A61M 39/22* (2006.01)

(52) U.S. Cl.

CPC ........ *A61M 39/22* (2013.01); *A61M 39/1011* (2013.01)

(58) Field of Classification Search

CPC . A61B 1/00105; A61B 1/0052; A61B 1/0057; A61B 8/4411; A61M 39/22
See application file for complete search history.

(56) References Cited

U.S. PATENT DOCUMENTS 6,017,322 A 1/2000 Snoke et al.
9,339,173 B2 5/2016 McWeeney et al.
9,757,537 B2 9/2017 Suon et al.
(Continued)

FOREIGN PATENT DOCUMENTS

DE 102019133463 6/2021
EP 0338557 A2 10/1989
(Continued)

OTHER PUBLICATIONS

International Search Report and Written Opinion issued in International Application No. PCT/US2022/036853, issued Oct. 31, 2022 (10 pages).

*Primary Examiner* — Deanna K Hall
(74) *Attorney, Agent, or Firm* — Bookoff McAndrews, PLLC

(57) ABSTRACT

A medical device that includes a first body including a first actuation member including a first connector and a second actuation member. The medical device includes a second body for attachment to, and detachment from, the first body. The second body including an actuation wire, a second connector at a proximal end of the actuation wire, and a valve having one or more channels for receiving a material. Attachment of the first body with the second body results in the first connector engaging the second connector, such that movement of the first actuation member causes a corresponding movement of the actuation wire. Moving the second actuation member into the second body to interact with the valve is configured to selectively direct the material through the one or more channels.

20 Claims, 14 Drawing Sheets

(56) References Cited

U.S. PATENT DOCUMENTS

| | | | |
|---|---|---|---|
| 2010/0056867 | A1 | 3/2010 | Labombard et al. |
| 2017/0273545 | A1 | 9/2017 | Dong et al. |
| 2019/0298897 | A1 | 10/2019 | Attinger |
| 2019/0313881 | A1 | 10/2019 | Francher |
| 2020/0046209 | A1 | 2/2020 | Francher |
| 2020/0221932 | A1 | 7/2020 | OuYang et al. |
| 2022/0151463 | A1 | 5/2022 | Francher et al. |

FOREIGN PATENT DOCUMENTS

| | | | |
|---|---|---|---|
| WO | WO 2021/026231 | | 2/2021 |
| WO | WO 2022/109488 | A1 | 5/2022 |
| WO | WO 2022/125550 | A1 | 6/2022 |

MODULAR MEDICAL DEVICES AND METHODS OF USING THE SAME

CROSS-REFERENCE TO RELATED APPLICATIONS

This application claims the benefit of priority of U.S. Provisional Patent Application No. 63/221,426, filed Jul. 13, 2021, the entirety of which is incorporated herein by reference.

TECHNICAL FIELD

Various aspects of this disclosure relate generally to modular medical systems, devices, and related methods. For example, the disclosure includes systems, devices, and related methods for utilizing a modular medical device including reusable and disposable components to treat a target site of a subject.

BACKGROUND

Certain medical devices may be utilized in numerous procedures for treating multiple patients. Prior to reuse, such medical devices may undergo extensive sterilization and/or reprocessing procedures to safely prepare the device for use in a subsequent procedure. However, despite extensive cleaning measures, cross-contamination between patients may still occur from the reuse of medical devices across multiple procedures, thereby resulting in possible infection and other post-procedure complications for the patient. Disposable medical devices may be employed in lieu of reusable medical devices, however, providing for a single use of components may result in increased costs. Medical devices that may be reusable or disposable to provide a balance between minimizing contamination and saving costs may be limited.

SUMMARY

Aspects of the disclosure relate to, among other things, systems, devices, and methods for a modular medical device including disposable and reusable components, among other aspects. Each of the aspects disclosed herein may include one or more of the features described in connection with any of the other disclosed aspects.

According to an example, a medical device includes a first body including: a first actuation member including a first connector; and a second actuation member; a second body for attachment to, and detachment from, the first body, the second body including: an actuation wire; a second connector at a proximal end of the actuation wire; and a valve having one or more channels for receiving a material; wherein attachment of the first body with the second body results in the first connector engaging the second connector, such that movement of the first actuation member causes a corresponding movement of the actuation wire; and wherein moving the second actuation member into the second body to interact with the valve is configured to selectively direct the material through the one or more channels.

Any of the medical devices described herein may include any of the following features. The second actuation member is configured to close an opening of at least one of the one or more of channels by at least partially deforming the valve at the opening. The second body includes a movable valve body disposed within the valve, the movable valve body being biased to a first position by a biasing mechanism positioned against the movable valve body. The second actuation member is configured to compress the biasing mechanism and move the movable valve to a second position. The first body includes a channel and the second body includes a fluidics tube configured to receive the material from a source, wherein the channel is configured to receive the fluidics tube through the first body. The first body includes an actuator coupled to the first actuation member, and the second body includes a shaft coupled to a distal end of the actuation wire. The actuator is configured to articulate the shaft in response to actuator moving the first actuation member, and the first actuation member moving the actuation wire, when the first connector is engaged with the second connector. The first connector includes a grasper, and the second connector includes a pair of pins defining a gap sized to receive the grasper between the pair of pins. The grasper is configured to engage the pair of pins by extending through the gap to couple the first actuation member to the actuation wire. The grasper is configured to extend through the gap in response to the first body rotating in a first direction relative to the second body when the first body is at least partially received within the second body. The grasper is configured to disengage the pair of pins from the grasper in response to the first body rotating in a second direction relative to the second body that is opposite of the first direction. The actuation wire is configured to move relative to the second body in response to the first actuation member moving relative to the first body. The first body includes an actuator coupled to a gear, and the first actuation member includes a gear rack configured to mesh with the gear. The actuator is configured to translate the first actuation member and the first connector by rotating the gear. Further including a locking mechanism having a pin on the first body, and an aperture on the second body that is configured to receive the pin when the first body is received within, and rotated relative to, the second body, thereby fixing an axial position of the first body relative to the second body.

According to another example, a medical device includes a proximal handle including: a handle housing including a channel; an actuation rod disposed within and movable relative to the handle housing; an actuator movably coupled to the actuation rod; and a shaft assembly including: a shaft housing including a fluidics tube extending proximally from the shaft housing, the fluidics tube configured to extend through the channel of the handle housing; a valve manifold disposed within the shaft housing; and at least one fluidics channel defined by the valve manifold and in fluid communication with the fluidics tube; wherein the actuator is configured to control the fluid communication between the at least one fluidics channel and the fluidics tube by abutting the actuation rod against the valve manifold to at least partially deform the valve manifold.

Any of the medical devices described herein may include any of the following features. The valve manifold includes a movable valve body and a biasing mechanism disposed within the valve manifold, wherein the movable valve body is biased to a default position when the biasing mechanism is in an expanded configuration; and wherein the at least one fluidics channel is in fluid communication with the fluidics tube when the movable valve body is in the default position. The actuator is configured to move the movable valve body to an actuated position by urging the biasing mechanism to a compressed configuration; wherein the at least one fluidics channel is not in fluid communication with the fluidics tube when the movable valve body is in the actuated position. The proximal handle includes a first connector and a second actuation rod coupled to the first connector, the first connector is movable relative to the handle housing in response to movement of the second actuation rod, and the shaft assembly includes a second connector and an actuation wire coupled to the second connector, the second connector is movable relative to the shaft housing in response to movement of the actuation wire; and wherein the second actuation rod is configured to move the actuation wire when the first connector is mated with the second connector.

According to a further example, a medical device includes a first body including: an actuator; a movable rod coupled to the actuator and configured to move in response to actuation of the actuator; and a second body selectively attachable to the first body, the second body including: a valve having a flexible body; and a plurality of channels configured to deliver a material through the second body; wherein the actuator is configured to selectively divert the material through the plurality of channels in response to moving the movable rod against the valve to at least partially deform the flexible body.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
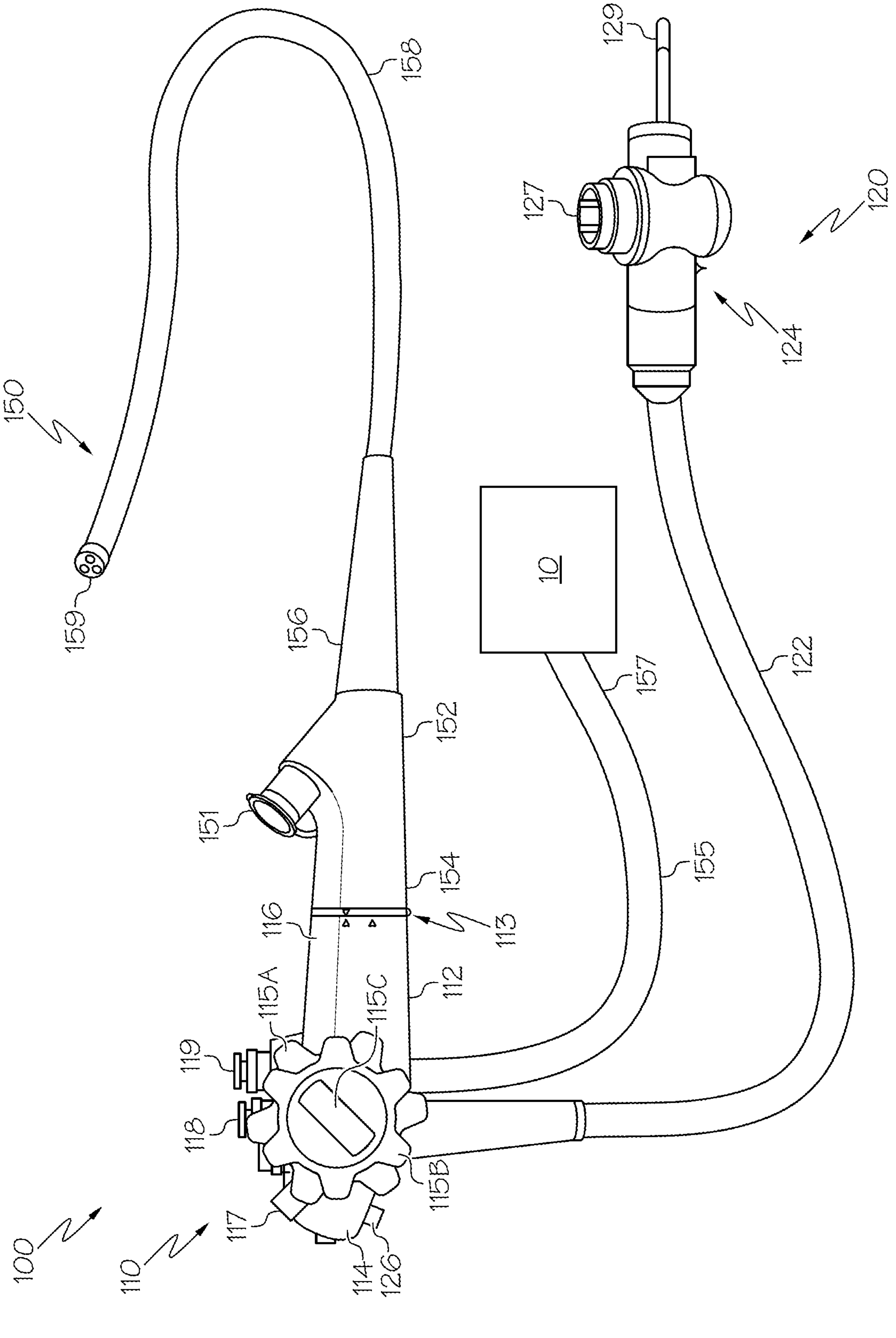
FIG. 1 is a perspective view of an exemplary medical device including a reusable body and a disposable body, according to aspects of this disclosure.

This disclosure relates, in certain aspects, to modular medical devices with reusable and disposable components. In some procedures, reuse of a medical device (e.g., endoscope) that was previously utilized in a prior procedure for a same or different patient may be common after the device has undergone sterilization and/or reprocessing measures. Such measures may be generally costly and imperfect as subsequent patients may be at an increased risk to sustain ailments (e.g., infection) resulting from cross-contamination of the device from a prior medical procedure. Employing single-use medical devices may minimize instances of utilizing contaminated devices in subsequent procedures, however, disposal of single-use devices may not provide an efficient balance of saving costs and minimizing contamination.

Examples of the disclosure include systems, devices, and methods for a modular medical device including a reusable body (e.g., handle) and a disposable body (e.g., tube) for treating a target treatment site within a subject (e.g., patient). The reusable body may be positioned external to the target treatment site during a procedure, such that contamination of the reusable body may be minimized, thereby allowing for the reusable body to be reutilized in subsequent procedures with a reduced risk of cross-contamination between patients. At least part of the disposable body may be received within the target treatment site during a procedure and disassembled from the reusable body upon completion of the procedure, thereby allowing for the disposal of the disposable body to minimize contamination of subsequent patients.

In examples, accessing a target treatment site may include endoluminal placement of the medical device into the patient, such as through an anatomical passageway via a natural orifice. The orifice can be, for example, the nose, mouth, or anus, and the placement can be in any portion of the GI tract, including the esophagus, stomach, duodenum, large intestine, or small intestine. Placement also can be in other organs or other bodily spaces reachable via the GI tract, other body lumens, or openings in the body. This disclosure is not limited to any particular medical procedure or treatment site within a body.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). As mentioned above, this disclosure is not limited to any specific medical device or method, and aspects of the disclosure may be used in connection with any suitable medical tool and/or medical method, at any suitable site within the body.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

FIG. 1 shows an exemplary medical device 100 in accordance with one or more examples of this disclosure. Medical device 100 may include a first (reusable) body 110, an umbilicus assembly 120, and a second (disposable) body 150. Medical device 100 may have a modular configuration such that first body 110 and second body 150 may be selectively coupled and decoupled from one another, and first body 110 and umbilicus assembly 120 may be selectively coupled and decoupled from one another.

First body 110 and/or umbilicus assembly 120 may be configured such that first body 110 and/or umbilicus assembly 120 may be reusable across multiple procedures. Second body 150 may be configured such that second body 150 may be disposable after a single use. Accordingly, at least a portion of medical device 100 (e.g., second body 150) may be disassembled and discarded after use in a procedure. In some embodiments, first body 110 may be coupled to various second (disposable) bodies, each of which may be configured and operable for use in a particular procedure and/or anatomy of a subject.

Figure 2:
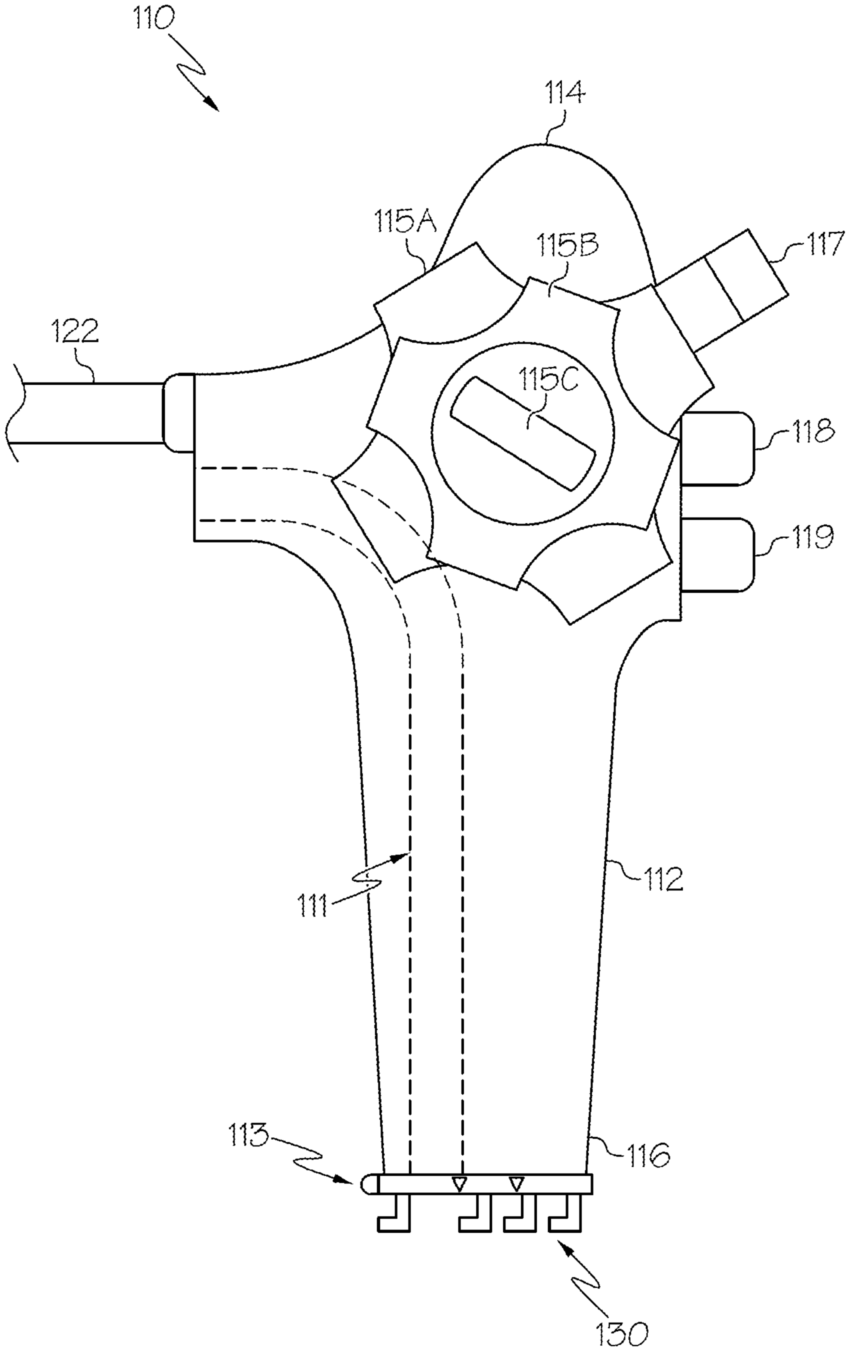
FIG. 2 is a partial side view of the reusable body of the medical device of FIG. 1, according to aspects of this disclosure.

Referring now to FIG. 2, first body 110 may define a reusable proximal handle including a housing 112 having a longitudinal length defined between a proximal end 114 and a distal end 116. First body 110 may include one or more control knobs movably coupled to housing 112 at proximal end 114. In the example, first body 110 may include a first control knob 115A, a second control knob 1156, and a third control knob 115C. First control knob 115A and second control knob 1156 may be coupled to and configured to control a movable actuation rod disposed within housing 112 (see FIG. 6). As described further herein, the movable actuation rods disposed within housing 112 may be coupled to one or more components of second body 150, such as a shaft 158, such that control knobs 115 may be configured to selectively move shaft 158 of second body 150 (e.g., articulate a distal portion of shaft 158). Third control knob 115C may be configured to selectively lock first control knob 115A and second control knob 1156 to a fixed position.

First body 110 may further a plurality of actuators (e.g., depressible buttons, rotatable knobs, etc.) at proximal end 114, such as, for example, a first actuator 117, a second actuator 118, and a third actuator 119. Each of the plurality of actuators may be coupled to and configured to control a corresponding movable rod disposed within housing 112 (see FIGS. 6 and 11). The movable rods disposed within housing 112 may be coupled to one or more components of second body 150, such as an elevator or a valve, such that the plurality of actuators may be configured to selectively actuate one or more of the elevator or the valve of second body 150. In the example, first actuator 117 may be coupled to an elevator of second body 150 positioned at a distal tip 159 of shaft 158 (see FIG. 1). Pivoting of actuator 117 may lift the elevator of second body 150. Second actuator 118 and third actuator 119 may selectively actuate a valve manifold 170 of second body 150 (see FIGS. 12A-12C) to establish fluid communication between first body 110, umbilicus assembly 120, second body 150, and/or an external device 10 fluidly coupled to medical device 100 (see FIG. 1).

Still referring to FIG. 2, first body 110 may include an internal channel 111 disposed within housing 112 and extending between proximal end 114 and distal end 116. Internal channel 111 may be sized and shaped to receive one or more components of second body 150, such as a fluidics tube assembly 155 (see FIG. 3). Distal end 116 may be configured to interface with second body 150 to couple first body 110 to second body 150. As shown and described in further detail herein, distal end 116 may be sized and shaped to be at least partially received within second body 150 for coupling first body 110 to second body 150, thereby assembling medical device 100.

Further, first body 110 may include a first connector assembly 130 disposed within housing 112 and extending distally from distal end 116. As described in detail below, first connector assembly 130 may be configured to mate with a corresponding connector assembly of second body 150 (e.g., a second connector assembly 160) to operably couple one or more components of first body 110 (e.g., control knobs 115, first actuator 117) with one or more components of second body 150 (see FIG. 6).

Figure 5A:
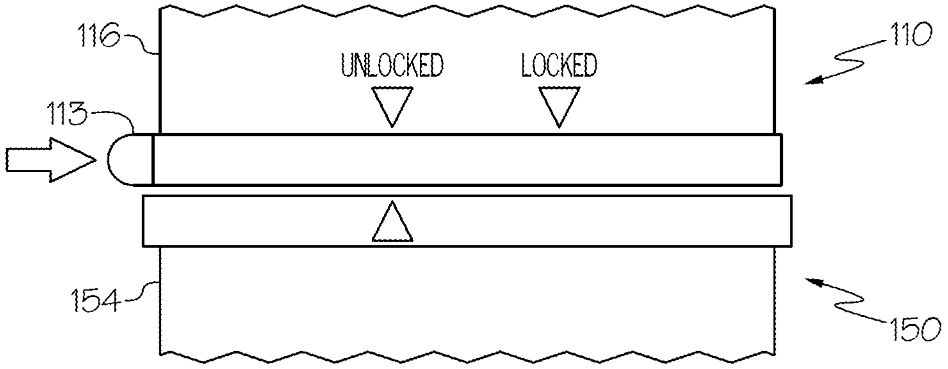
FIG. 5A is a partial side view of an interface between the reusable body and the disposable body of the medical device of FIG. 1, the medical device positioned in a decoupled state, according to aspects of this disclosure.
Figure 5B:
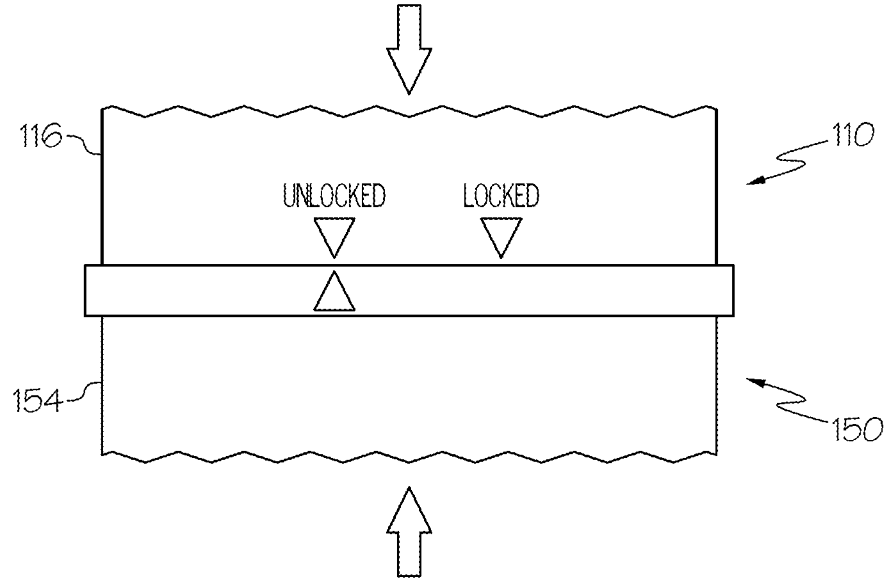
FIG. 5B is a partial side view of an interface between the reusable body and the disposable body of the medical device of FIG. 1, the medical device positioned in an unlocked state, according to aspects of this disclosure.
Figure 5C:
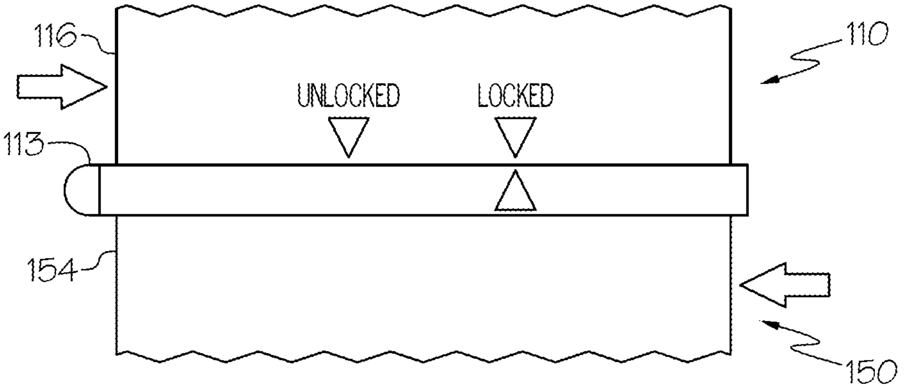
FIG. 5C is a partial side view of an interface between the reusable body and the disposable body of the medical device of FIG. 1, the medical device positioned in a locked state, according to aspects of this disclosure.

Medical device 100 may further include a locking mechanism for selectively securing first body 110 to second body 150 (see FIGS. 5A-5C). For example, the locking mechanism may include a depressible pin 113 disposed along distal end 116 of first body 110. As described in further detail herein, pin 113 may be biased radially outward from housing 112 by a biasing mechanism (e.g., spring) positioned against an interior surface of pin 113, such that pin 113 may be urged to an extended state absent application of a radially-inward force, such as from second body 150 when distal end 116 is received within second body 150.

Referring back to FIG. 1, umbilicus assembly 120 may include an umbilicus tube 122, an umbilicus connector 124, and a plurality of connections on umbilicus connector 124. Umbilicus tube 122 may include a plurality of channels (not shown) that are configured to receive one or more electronic cables (not shown) from umbilicus connector 124. The electronic cables may be configured to electrically couple to corresponding electronic cables of first body 110. In some embodiments, first body 110 may include first electronic cables (not shown) disposed within housing 112, and having an electrical connector terminating at, and accessible from, a port at proximal end 114 at which umbilicus tube 122 is received. The first electronic cables may be coupled to second electronic cables disposed within umbilicus assembly 120 by connecting the electrical connectors of the first electronic cables to corresponding electrical connectors of the second electronic cables.

For example, the electrical connectors of the first and second electronic cables may be manually connected to one another by a user of medical device 100. In other examples, the corresponding electrical connectors may automatically mate with one another when first body 110 is coupled to umbilicus assembly 120. Electronic devices and/or instruments (e.g., imaging devices, illumination devices, sensors, etc.) may be communicatively coupled to the electronic cables of umbilicus assembly 120 via the plurality of connectors on umbilicus connector 124. Umbilicus connector 124 may include at least a first connector 127 (e.g., a first device connection) for coupling an imaging device to medical device 100, and a second connector 129 (e.g., a second device connection) for coupling an illumination device to medical device 100.

In some embodiments, umbilicus assembly 120 and first body 110 may be integral components with one another, such that first body 110 and umbilicus assembly 120 may be fixedly attached to one another. In this instance, the electronic cables and/or wires from umbilicus connector 124 may extend through umbilicus tube 122 and housing 112. Suitable electronic connections and other circuitry may be disposed within housing 112 for an image capture functionality, such as, for example, by actuating a button 126.

Still referring to FIG. 1, second body 150 may define a disposable shaft assembly include a housing 152 having a longitudinal length defined between a proximal end 154 and a distal end 156. Second body 150 may include one or more ports 151 for facilitating access into housing 152, such as for receipt of one or more devices or instruments. Stated differently, the one or more ports 151 may be sized, shaped, and configured to receive one or more devices (not shown) into second body 150, such as, for example, a sample collection device, a biopsy forceps, a grasper, or any other therapeutic or diagnostic tool. In the example, biological matter (e.g., biohazardous fluids) extracted from a target treatment site by medical device 100 may be collected at a sample collection device coupled to second body 150 at port 151. Accordingly, first body 110 and umbilicus assembly 120 may be may be isolated from receiving such biological matter, thereby minimizing a potential contamination of said reusable components of medical device 100.

With one or more ports 151 located on second body 150 (as opposed to first body 110), it should be appreciated that fewer devices may be traversed through housing 112, thereby minimizing a wear and tear of first body 110 (i.e., the reusable handle). In the example, at least one port 151 may be positioned along housing 152 adjacent to distal end 156. Second body 150 may further include a flexible shaft 158 extending distally from distal end 156, and flexible shaft 158 may include distal tip 159 from which the one or more devices received in second body 150 may exit shaft 158.

Figure 3:
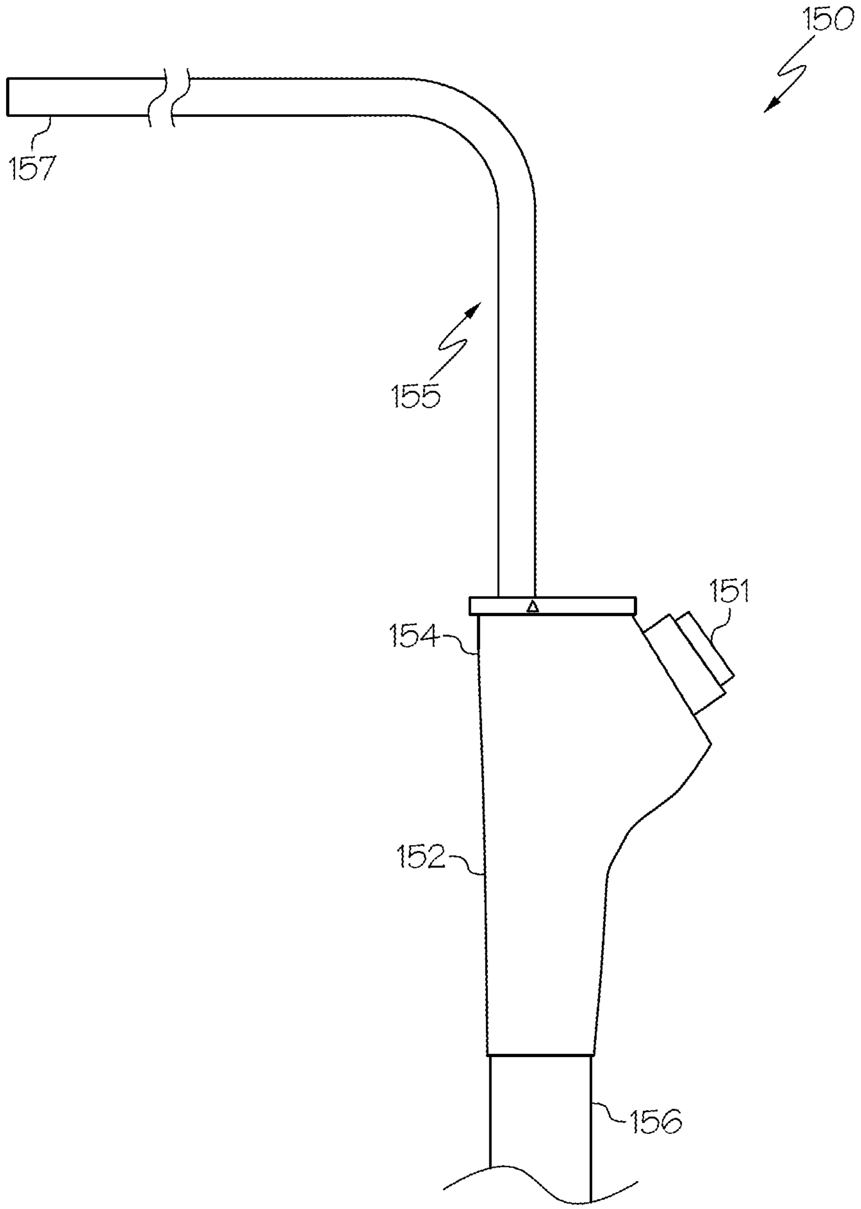
FIG. 3 is a partial side view of the disposable body of the medical device of FIG. 1, according to aspects of this disclosure.

Referring now to FIG. 3, second body 150 may include a (disposable) fluidics tube assembly 155 coupled to housing 152 at proximal end 154. Fluidics tube assembly 155 may include a flexible shaft extending proximally from proximal end 154. Fluidics tube assembly 155 may include one or more fluidics channels (not shown) extending between a first end of fluidics tube assembly 155 (coupled to housing 152) and a second end 157 of fluidics tube assembly 155 that is opposite of the first end. For example, fluidics tube assembly 155 may include a suction channel, a water channel, a pressurized air channel, and more. The one or more fluidics channels may be configured to receive and/or transmit various fluids during use of medical device 100, including, for example, water, air, saline, and more.

In some embodiments, second end 157 may be coupled to one or more external devices 10, such as, for example, a negative pressure medium source, a water supply source, a pressurized air source, etc. (see FIG. 1). External device 10 may include a plurality of nozzles (e.g., a suction valve nozzle for coupling the negative pressure medium source, a water valve nozzle for coupling the water supply, an air nozzle for coupling the pressurized air source, etc.). In this instance, fluids transmitted from and/or received by external device 10 may be isolated from first body 110 and umbilicus assembly 120 by delivering said fluids from and/or to external device 10 via fluidics tube assembly 155.

Figure 4:
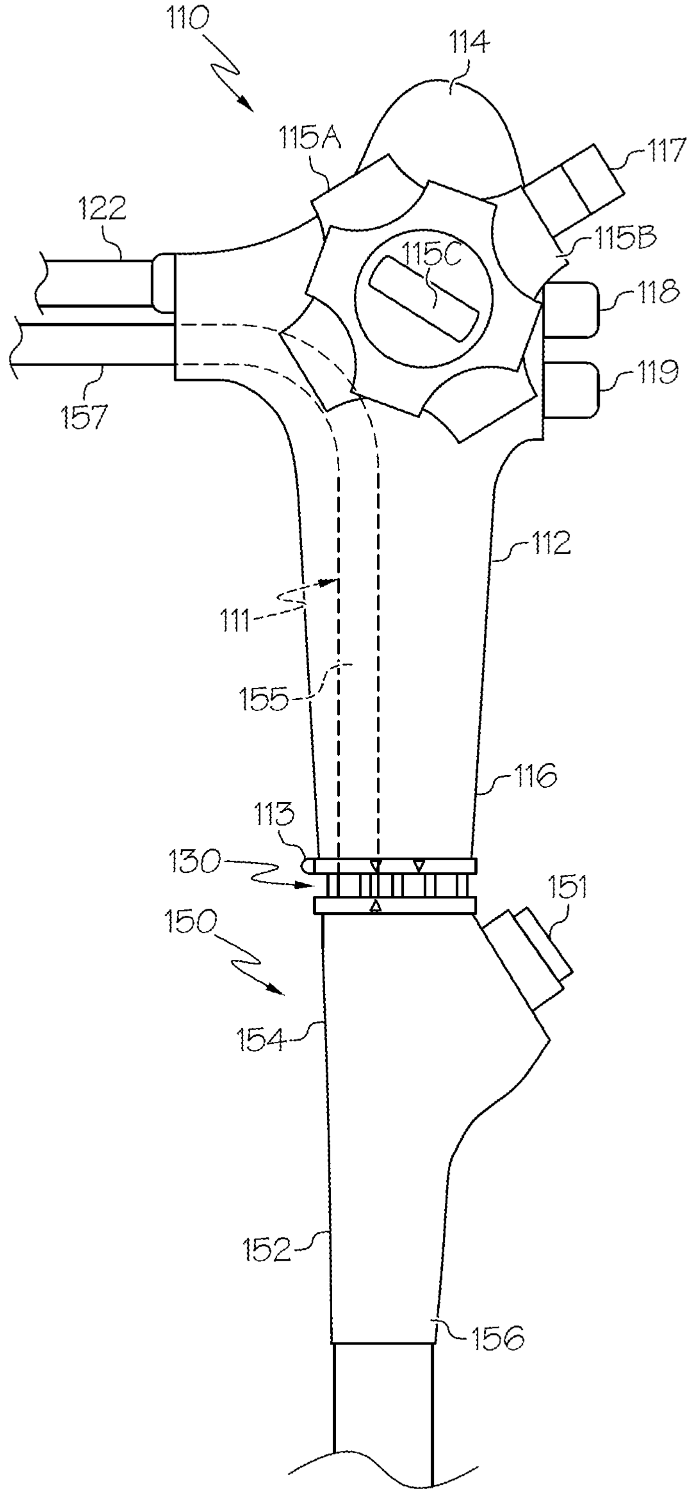
FIG. 4 is a partial side view of the reusable body coupled to the disposable body of the medical device of FIG. 1, according to aspects of this disclosure.

Referring to FIG. 4, fluidics tube assembly 155 may be sized, shaped, and configured to extend through housing 112 when first body 110 is coupled to second body 150, and particularly through internal channel 111. In the example, internal channel 111 may receive fluidics tube assembly 155 and second end 157 may extend outward from housing 112 at a location adjacent to proximal end 114 (e.g., via a port) to facilitate coupling of fluidics tube assembly 155 to external device 10. The plurality of fluidic channels of fluidics tube assembly 155 may be in fluid communication with one or more fluidic channels disposed within housing 152 and shaft 158, such as one or more corresponding suction channels, pressurized air channels, water channels, etc. As described in detail below, second actuator 118 and third actuator 119 may be configured to selectively connect and/or disconnect the one or more fluidic channels of fluidics tube assembly 155 with corresponding fluidics channels in shaft 158.

Accordingly, it should be appreciated that first body 110 and/or umbilicus assembly 120 may be isolated from receiving such fluids, thereby minimizing a potential contamination of said reusable components of medical device 100. Stated differently, only second body 150 (i.e. a disposable component) may be exposed to fluids during use of medical device 100, which may be disassembled from first body 110 and discarded after use in a procedure. By limiting first body 110 and umbilicus assembly 120 from exposure to fluids and/or biological matter, a sterilization and reprocessing of first body 110 and umbilicus assembly 120 may be unnecessary and/or minimized.

As briefly described above, medical device 100 may include a locking mechanism for attaching first body 110 to second body 150, with first body 110 including depressible pin 113. Second body 150 may include a groove (not shown) disposed along an interior surface of proximal end 154, and particularly along a proximal edge of proximal end 154, that aligns with a distal edge of distal end 116 when first body 110 is received within second body 150. The groove may be sized and shaped to receive depressible pin 113 when distal end 116 is received within proximal end 154.

Figure 9A:
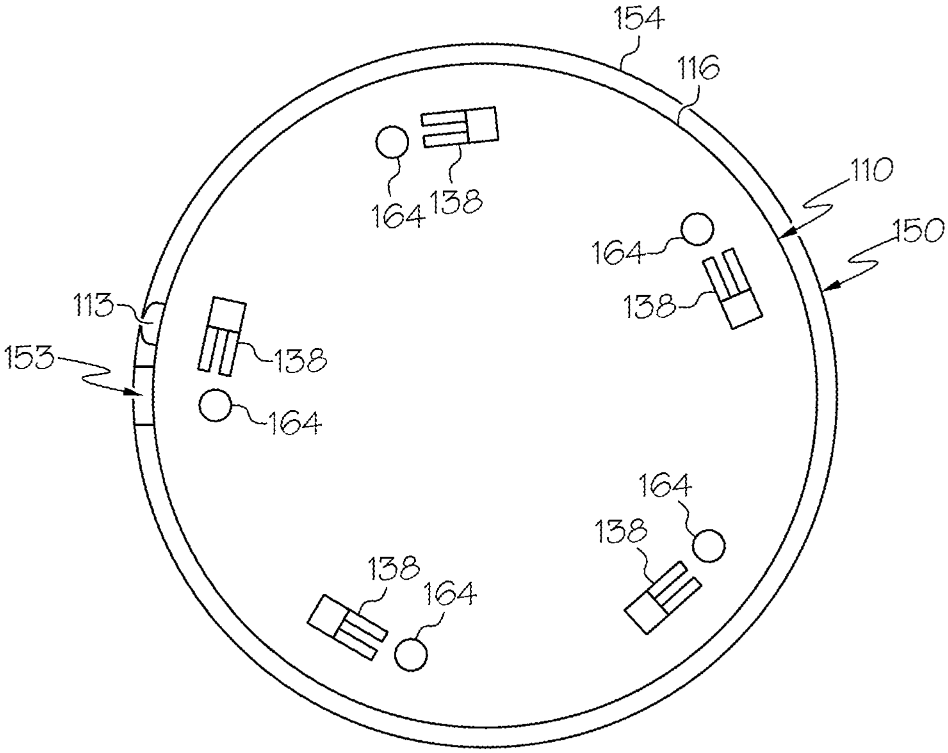
FIG. 9A is a cross-sectional view of the first connector assembly disengaged from the second connector assembly of the medical device of FIG. 1, according to aspects of this disclosure.
Figure 10A:
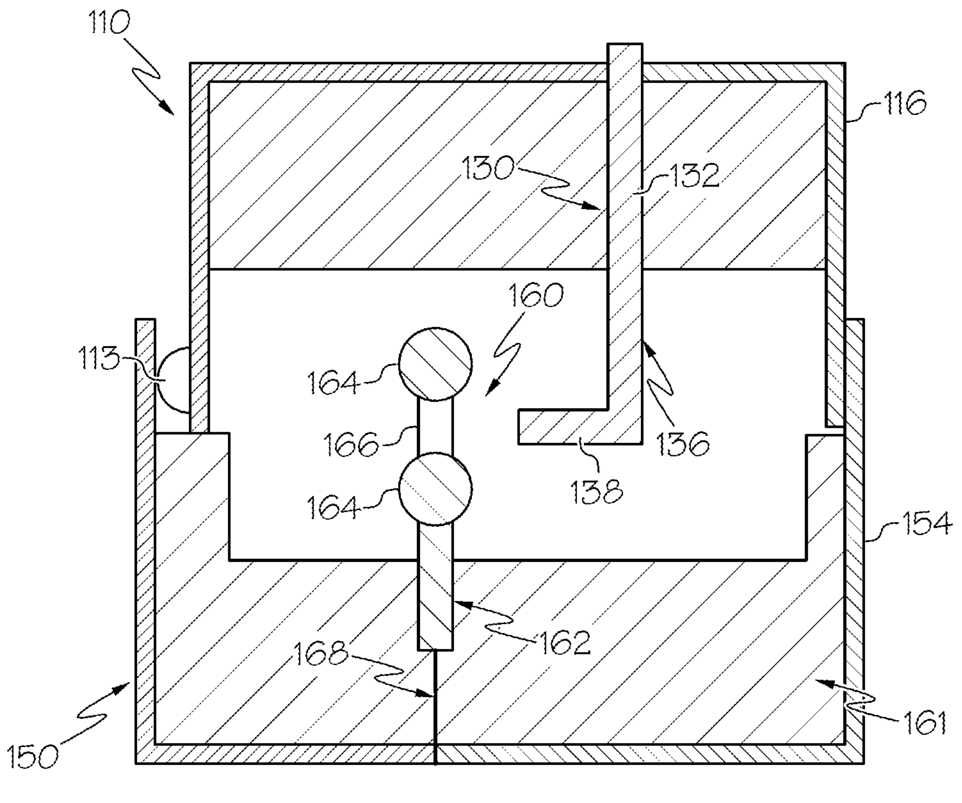
FIG. 10A is a partial cross-sectional view of the first connector assembly disengaged from the second connector assembly of the medical device of FIG. 1, according to aspects of this disclosure.

As seen in FIGS. 9A and 10A, depressible pin 113 may be disposed within second body 150, received within the groove at proximal end 154, and compressed radially-inward by the interior surface of proximal end 154 (against a radially-outward biasing force of a spring). Medical device 100 may be configured such that rotation of first body 110 relative to second body 150, or vice versa, may lock first body 110 to second body 150 when depressible pin 113 becomes aligned with an aperture 153 formed within the groove along the interior surface of proximal end 154.

Figure 9B:
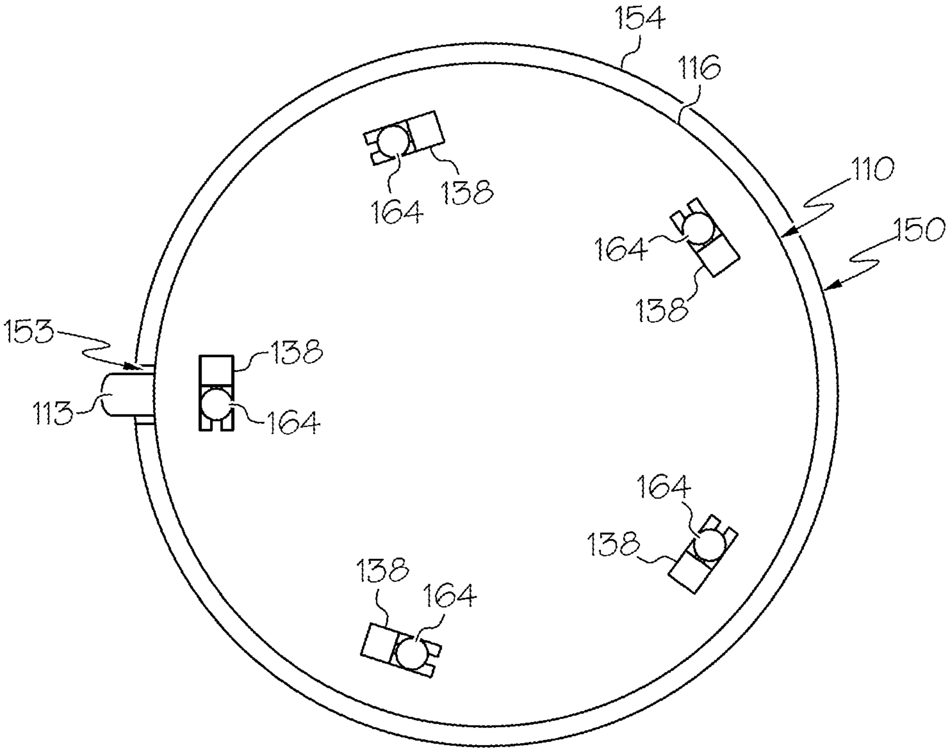
FIG. 9B is a cross-sectional view of the first connector assembly engaged to the second connector assembly of the medical device of FIG. 1, according to aspects of this disclosure.
Figure 10B:
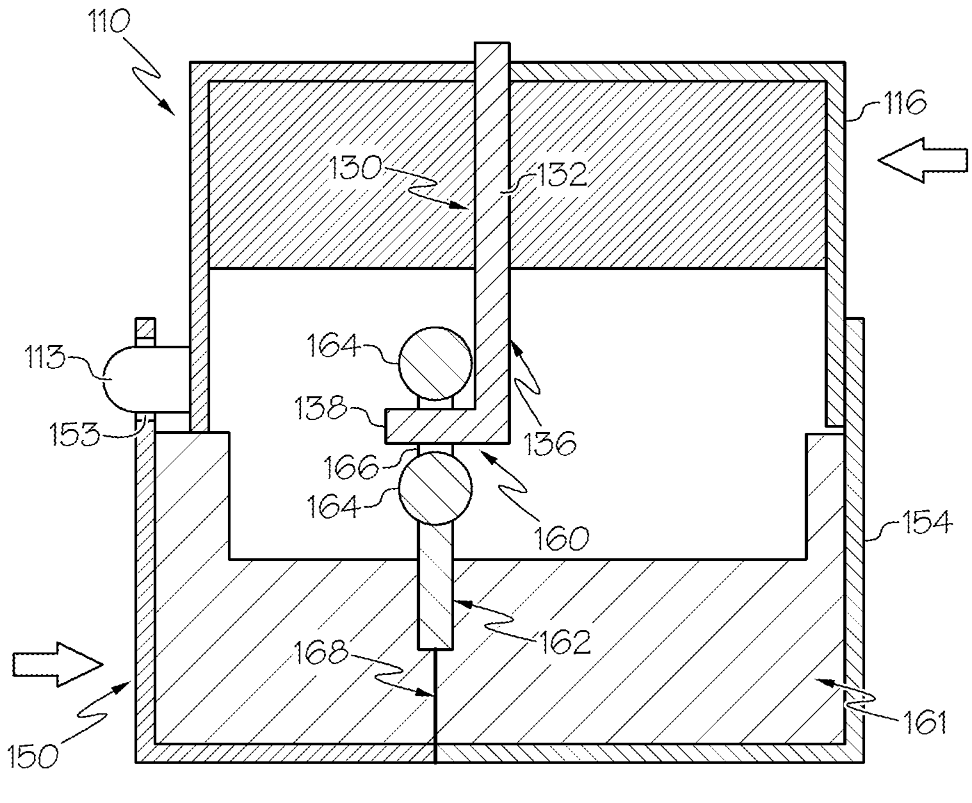
FIG. 10B is a partial cross-sectional view of the first connector assembly engaged to the second connector assembly of the medical device of FIG. 1, according to aspects of this disclosure.

As seen in FIGS. 9B and 10B, depressible pin 113 may extend radially-outward from first body 110 and through second body 150 when aligned with aperture 153. In this instance, the radially-outward biasing force of the spring urges depressible pin 113 through aperture 153. With depressible pin 113 received through aperture 153, first body 110 may be axially and rotationally fixed relative to second body 150. As described in further detail herein, rotation of first body 110 relative to second body 150, or vice versa, may couple one or more other components of first body 110 with components of second body 150, such as a first connector assembly 130 and second connector assembly 160.

Referring now to FIGS. 5A-5C, medical device 100 may include one or more markings along first body 110 and second body 150 to facilitate a visual identification of when the locking mechanism of medical device 100 is in an unlocked state and a locked state, respectively. As seen in FIG. 5A, when first body 110 is decoupled from second body 150, depressible pin 113 may be in an extended state protruding radially-outward from distal end 116. A user of medical device 100 may align the markings on first body 110 and second body 150 to insert first body 110 into second body 150.

As seen in FIG. 5B, in response to urging first body 110 into second body 150, depressible pin 113 may be compressed radially-inward and received within the groove positioned along the proximal edge of proximal end 154. In some embodiments, depressible pin 113 may be compressed as a result of second body 150 urging depressible pin 113 inward as distal end 116 is received within proximal end 154. In other embodiments, a user of medical device 100 may manually depress depressible pin 113 (e.g., using a hand of the user) to facilitate receipt of first body 110 into second body 150. With depressible pin 113 received within the groove of second body 150, medical device 100 remains in an unlocked state such that retraction of first body 110 may decouple second body 150 from first body 110.

As seen in FIG. 5C, in response to rotating first body 110 relative to second body 150 (or vice versa), depressible pin 113 may translate through the groove until aligning with the aperture on the proximal edge of proximal end 154. In this instance, depressible pin 113 may be received within the aperture and extend radially-outward through second body 150 at proximal end 154. In this instance, medical device 100 may be transitioned to a locked state such that first body 110 may be fixedly attached to second body 150. Medical device 100 may be returned to the unlocked state in response to manually depressing depressible pin 113 radially-inward into second body 150 and rotating first body 110 and/or second body 150 relative to one another to misalign depressible pin 113 with the aperture.

Figure 6:
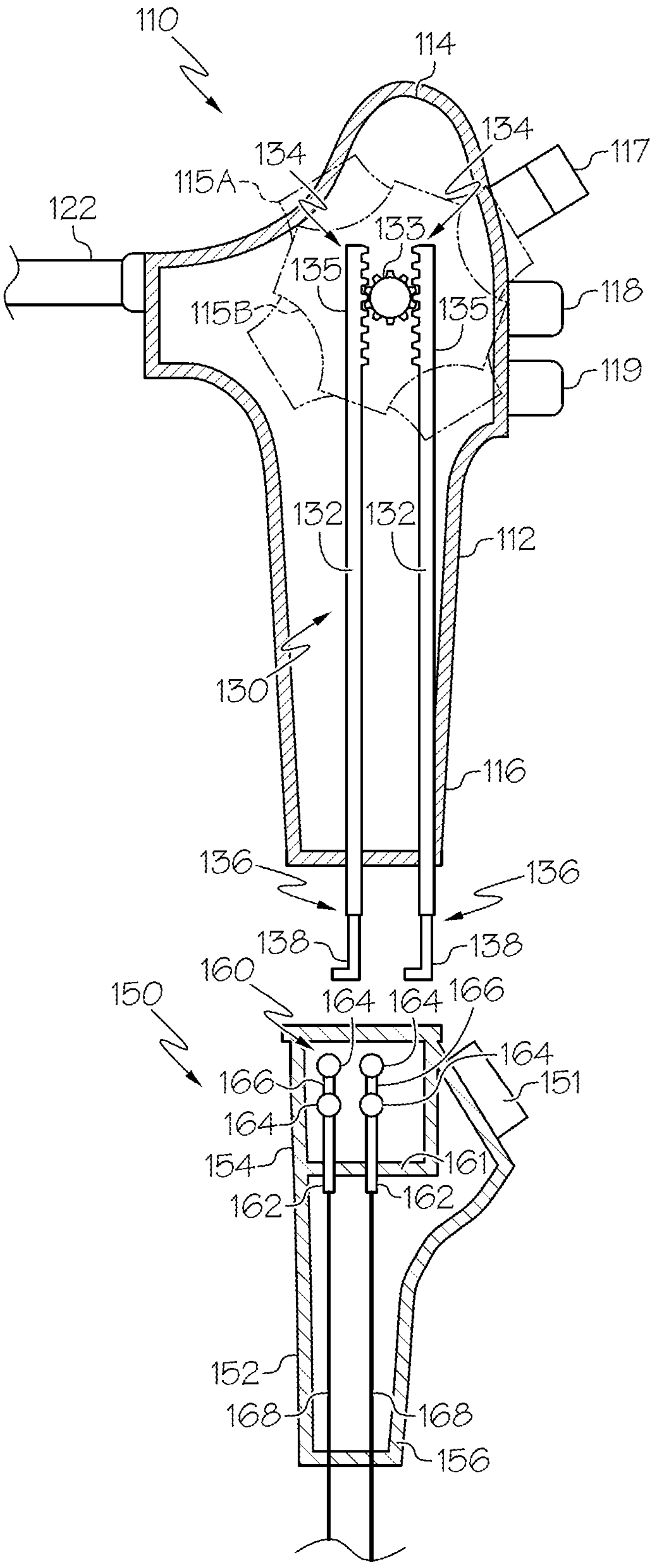
FIG. 6 is a cross-sectional side view of the reusable body and the disposable body of the medical device of FIG. 1, the reusable body including a first connector assembly and the disposable body including a second connector assembly, according to aspects of this disclosure.

Referring now to FIG. 6, medical device 100 may further include one or more connector assemblies for operably coupling one or more components of first body 110 (e.g., control knobs 115, first actuator 117) with one or more components of second body 150 (e.g., shaft 158, distal tip 159, etc.). In the example, first body 110 may include first connector assembly 130, and second body 150 may include a second connector assembly 160. First connector assembly 130 may include a plurality of movable rods 132 (actuation members) disposed within housing 112, and movable relative to first body 110.

The plurality of movable rods 132 each has a longitudinal length defined between a proximal end 134 and a distal end 136. Proximal ends 134 of the plurality of movable rods 132 may have a gear rack 135 along an interior side of each movable rod 132. The gear rack 135 of each movable rod 132 may be configured to mesh with a gear 133 movably coupled to at least one of the plurality of control knobs 115 and/or first actuator 117, and particularly a plurality of teeth of gear 133. Stated differently, movable rods 132, and particularly gear rack 135, and gear 133 may form a rack and pinion assembly with one another. Accordingly, the plurality of movable rods 132 may be configured to move (e.g., translate) relative to first body 110 in response to a rotation of a control knob 115A, 115B and/or first actuator 117 relative to first body 110. In the example, each control knob 115A, 115B may be coupled to at least one gear 133, and each gear 133 may be coupled to a pair of movable rods 132 for articulating shaft 158 in multiple directions (e.g., vertical articulation and lateral articulation). First actuator 117 may be coupled to a corresponding gear 133 that is further coupled to one movable rod 132 for actuating (e.g., lifting) the elevator at distal tip 159.

Still referring to FIG. 6, each of the plurality of movable rods 132 may further include a grasper tool 138 at distal end 136. Grasper tool 138 may include various suitable mechanisms for facilitating a connection between first connector assembly 130 and second connector assembly 160. For example, grasper tool 138 may include a hook, an arm, a clip, and/or various other suitable structures. In the example, first body 110 may be configured such that at least a portion of first connector assembly 130, and particularly grasper tools 138, may extend at least partially outward from distal end 116 to interface with second connector assembly 160 when first body 110 is received within second body 150. In other embodiments, first connector assembly 130 may be entirely disposed within housing 112.

Second connector assembly 160 may include a plurality of movable rods 162 corresponding to the number of movable rods 132 of first connector assembly 130. Each of the plurality of movable rods 162 may include a pair of pins 164 at a proximal end of movable rods 162, with the pair of pins 164 separated from one another by a gap 166 therebetween. Gap 166 may be sized and shaped in accordance with a cross-sectional profile of grasper tool 138, such that the pair of pins 164 is configured to receive grasper tool 138 within gap 166 to operably couple second connector assembly 160 to first connector assembly 130.

Still referring to FIG. 6, second connector assembly 160 may further include a plurality of actuation cables or wires 168 coupled to a distal end of the plurality of movable rods 162. In some embodiments, the plurality of movable rods 162 may be omitted entirely such that the plurality of wires 168 may be coupled directly to a distalmost pin 164 of the pair of pins 164. The plurality of wires 168 may extend through housing 152 and a lumen of shaft 158. A distal end of at least a subset of the plurality of wires 168 may be coupled to a distal portion of shaft 158, and particularly along an internal surface of shaft 158 (e.g., an articulating joint) positioned adjacent to distal tip 159. A distal end of at least one of the plurality of wires 168 may be coupled to a device at distal tip 159, such as an elevator (not shown).

In some embodiments, second body 150 may include a floor 161 disposed within housing 152 and positioned proximate to proximal end 154. Floor 161 may define a proximal cavity within housing 152 in which the plurality of pins 164 of second connector assembly 160 are housed. Floor 161 may be configured to maintain the plurality of pins 164 within the proximal cavity prior to an assembly of first body 110 to second body 150 to inhibit distal retraction of second connector assembly 160 into housing 152. In other words, floor 161 may hold the plurality of pins 164 within housing 152 in an area adjacent to proximal end 154 to facilitate connection between second connector assembly 160 and first connector assembly 130.

Still referring to FIG. 6, floor 161 may include a plurality of openings extending therethrough for receiving the plurality of movable rods 162 and/or wires 168. In response to first connector assembly 130 engaging second connector assembly 160, first body 110 may be configured to move (e.g., via control knobs 115 and first actuator 117) the plurality of movable rods 162 and/or wires 168 relative to second body 150 in response to movement of the plurality of movable rods 132 within first body 110. It should be appreciated that the plurality of movable rods 162 and/or wires 168 may move through the corresponding openings in floor 161 when second connector assembly 160 is actuated by first connector assembly 130. Floor 161 may be further configured to serve as a stop that limits the amount of distal translation of each wire 168. In other embodiments, first connector assembly 130 and second connector assembly 160 may be interchanged with one another such that first body 110 may include second connector assembly 160 and second body 150 may include first connector assembly 130.

Figure 7:
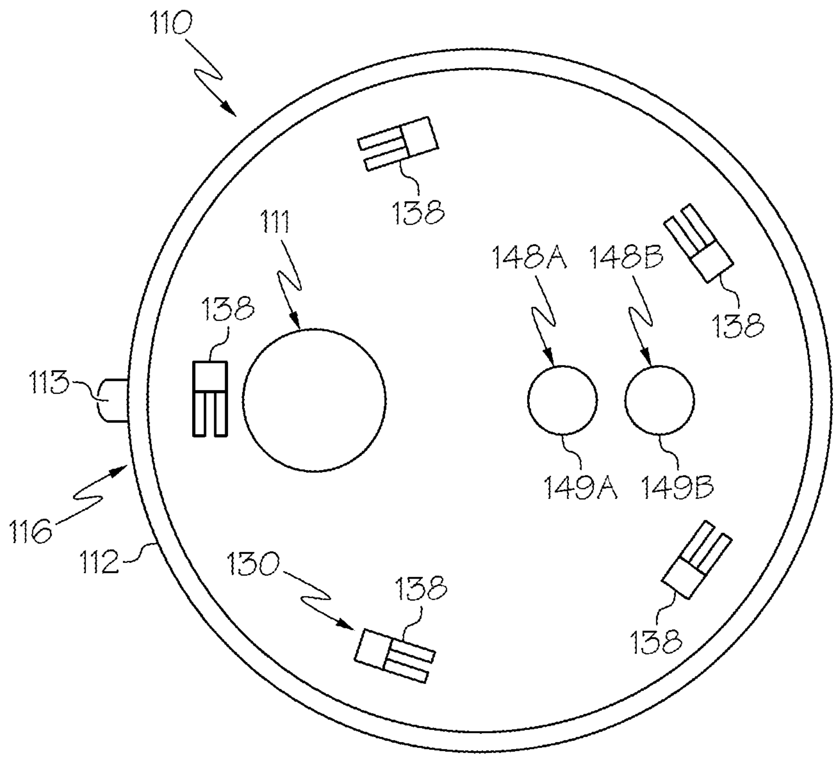
FIG. 7 is a bottom view of the reusable body of the medical device of FIG. 1, with the first connector assembly disposed within the reusable body, according to aspects of this disclosure.

FIG. 7 shows distal end 116 of first body 110 and the one or more components disposed within housing 112, including the plurality of grasper tools 138 of first connector assembly 130 and internal channel 111. The plurality of grasper tools 138 may be disposed within first body 110 in an annular array about an internal perimeter of housing 112. It should be appreciated that the plurality of grasper tools 138 may be positioned within housing 112 in various other suitable arrangements than that shown and described herein without departing from a scope of this disclosure. In the example, first body 110 may include five grasper tools 138, a first pair of which may be coupled to a first control knob 115A for controlling a lateral (e.g., left-right) articulation of shaft 158, a second pair of which may be coupled to a second control knob 1156 for controlling a vertical (e.g. up-down) deflection of shaft 158, and a fifth grasper tool 138 may be coupled to first actuator 117 for controlling an elevator at distal tip 159.

Figure 11:
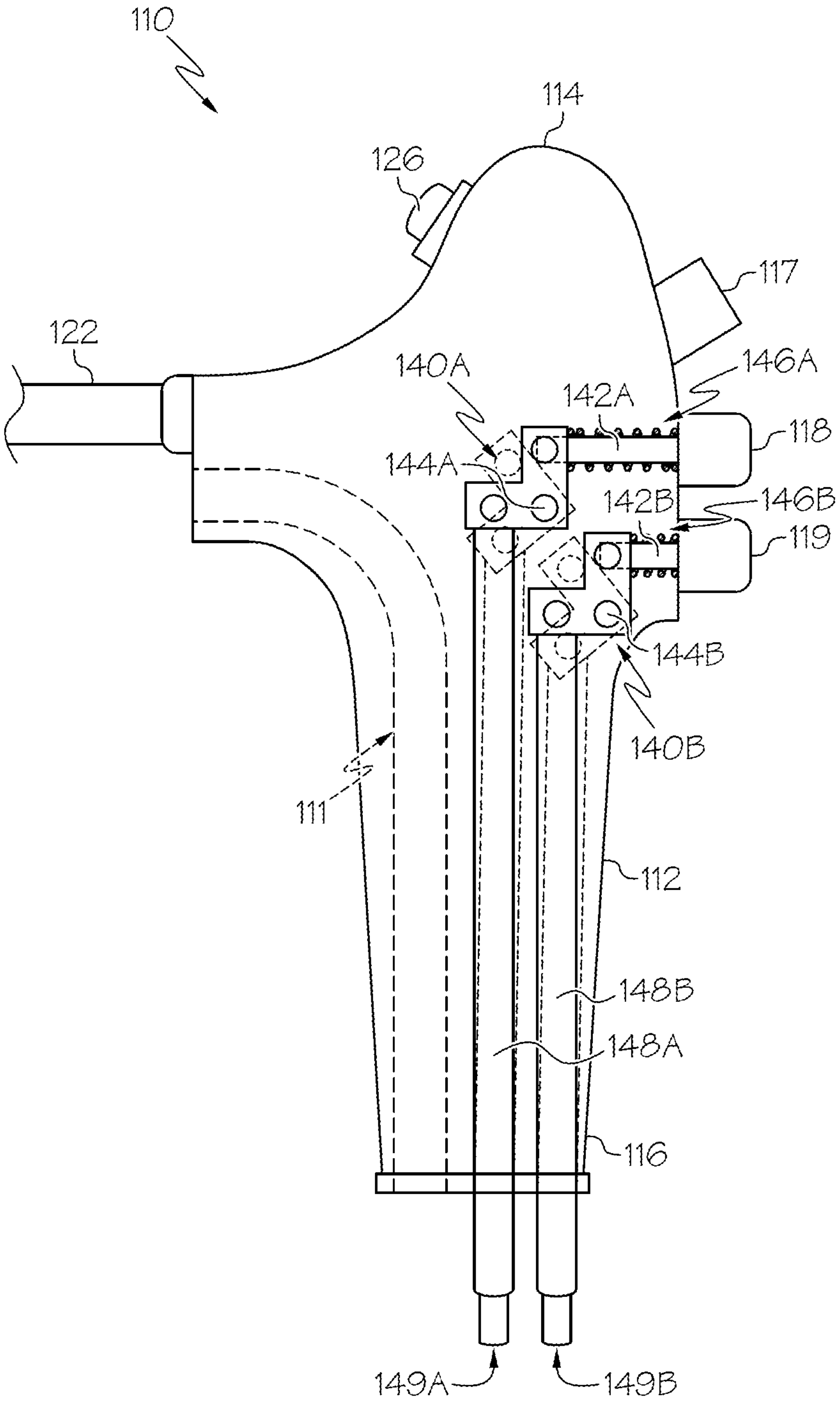
FIG. 11 is a partial cross-sectional view of the reusable body of the medical device of FIG. 1 including a plurality of actuators, according to aspects of this disclosure.

First body 110 may further include a plurality of movable rods 148 (actuation members) disposed within housing 112 for controlling one or more components of second body 150 (e.g., a valve manifold 170). In the example, first body 110 may include at least a first movable rod 148A having a distal end 149A and a second movable rod 148B having a distal end 149B. In other embodiments, first body 110 may include additional and/or fewer movable rods. As described in further detail herein, first movable rod 148A may be movably coupled to second actuator 118, and second movable rod 148B may be movably coupled to second actuator 119 (FIG. 11).

Figure 8:
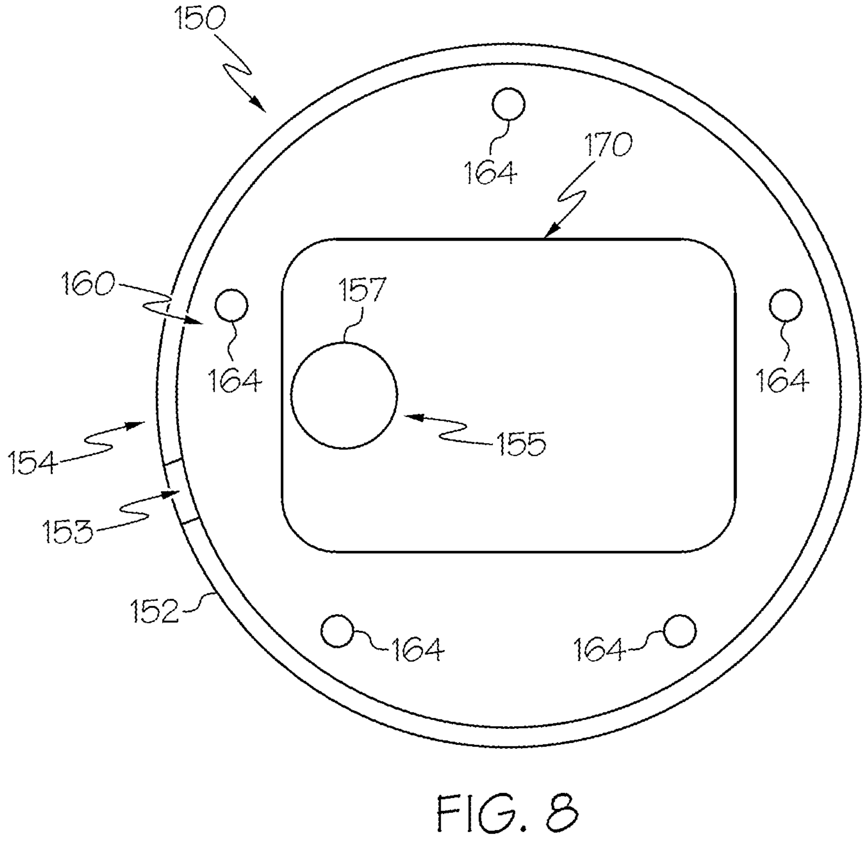
FIG. 8 is a top view of the disposable body of the medical device of FIG. 1, with the second connector assembly disposed within the disposable body, according to aspects of this disclosure.

FIG. 8 shows proximal end 154 of second body 150 and the one or more components disposed within housing 152, including the plurality of pins 164 of second connector assembly 160 and fluidics tube assembly 155. The plurality of pins 164 may be disposed within second body 150 in an annular array about an internal perimeter of housing 152. It should be appreciated that the plurality of pins 164 may be positioned within housing 152 in various other suitable arrangements in accordance with a corresponding position of the plurality of grasper tools 138 within first body 110.

Second body 150 may further include a valve manifold 170 positioned proximate to proximal end 154. As described in further detail below, valve manifold 170 may be configured to interact with one or more of the plurality of movable rods 148 of first body 110 to control fluid communication between a plurality of fluidics channels of valve manifold 170 (see FIGS. 12A-12C). For example, movable rods 148 may be configured to selectively divert fluid through the plurality of fluidics channels of valve manifold 170.

As seen in FIG. 9A, with distal end 116 received within proximal end 154, the plurality of grasper tools 138 may be located proximate to the plurality of pins 164. For example, FIG. 10A shows each distal end 136 of first connector assembly 130 positioned adjacent to the pair of pins 164 of second connector assembly 160 with each grasper tool 138 positioned in alignment with gap 166. A position of grasper tools 138 relative to pins 164 may correspond to an orientation of first body 110 relative to second body 150 when distal end 116 is received within proximal end 154 (see FIG. 5B). Accordingly, movement (e.g., rotation) of first body 110 and/or second body 150 relative to one another may move one or more of grasper tool 138 and/or the pair of pins 164 toward one another. Additionally, depressible pin 113 may be received against an interior surface (e.g., groove) of second body 150 at proximal end 154, thereby compressing depressible pin 113 radially-inward.

As seen in FIG. 9B, with first body 110 rotated relative to second body 150 to a locked position (see FIG. 5C), the position of grasper tools 138 and pins 164 may facilitate a connection between first connector assembly 130 and second connector assembly 160. For example, FIG. 10B shows each of the plurality of grasper tools 138 engaging the pair of pins 164 by extending through gap 166. In this instance, first connector assembly 130 and second connector assembly 160 may operably couple control knobs 115 and first actuator 117 to wires 168. Additionally, depressible pin 113 may move along the groove along the interior surface of proximal end 154 until aligning with aperture 153, thereby extending through aperture 153 and securely coupling first body 110 to second body 150. In this instance, first body 110 may be axially and rotatably fixed relative to second body 150.

FIG. 11 shows a corresponding connection between actuators 118, 119 on proximal end 114 of first body 110 and a corresponding movable rod (actuation member) disposed within housing 112. As described in detail above, first body 110 may include second actuator 118 movably coupled to first movable rod 148A and third actuator 119 movably coupled to second movable rod 148B. In the example, first body 110 may include a coupling mechanism configured to connect each actuator with the corresponding movable rod.

For example, second actuator 118 may be movably coupled to a coupling mechanism 140A via an intermediate rod 142A extending between second actuator 118 and coupling mechanism 140A. Intermediate rod 142A may be coupled to coupling mechanism 140A at a first end, and may include a biasing mechanism 146A coupled to intermediate rod 142A. Biasing mechanism 146A may be configured to apply a radially-outward force against second actuator 118, thereby urging second actuator 118 to an extended (unactuated) position when in a default state.

Still referring to FIG. 11, first movable rod 148A may be directly coupled to coupling mechanism 140A along a second end that is different than the first end, and distal end 149A of first movable rod 148A may be positioned in a proximal (retracted) state when second actuator 118 is in the extended (unactuated) position. Coupling mechanism 140A may be configured to move (e.g., translate) first movable rod 148A relative to housing 112 in response to an actuation (e.g., depression) of second actuator 118, thereby positioning distal end 149A in a distal (extended) state.

In this instance, actuation of second actuator 118 may cause a compression of biasing mechanism 146A, and a translation of intermediate rod 142A and corresponding movement of coupling mechanism 140A about a fixed pivot pin 144A between the opposing first and second ends. In response to coupling mechanism 140A moving (e.g., pivoting) about fixed pivot pin 144A, first movable rod 148A may move (e.g., translate) distally from first body 110 in a direction that is transverse from a (lateral) translation of intermediate rod 142A.

Still referring to FIG. 11, third actuator 119 may be movably coupled to a coupling mechanism 140B that is substantially similar to coupling mechanism 140A shown and described above. For example, second movable rod 148B may be directly coupled to coupling mechanism 140B, and third actuator 119 may be coupled to coupling mechanism 140B via an intermediate rod 142B and a biasing mechanism 146B positioned therebetween. Coupling mechanism 140B may be configured to move (e.g. pivot) about a fixed pivot pin 144B to translate second movable rod 148A and distal end 149B. Accordingly, third actuator 119 and second movable rod 148B may be configured and operable similar to second actuator 118 and first movable rod 148A, respectively. As described in further detail herein, distal end 149A of first movable rod 148A and distal end 149B of second movable rod 148B may be configured to interact with valve manifold 170 when first body 110 is coupled to second body 150.

Figure 12A:
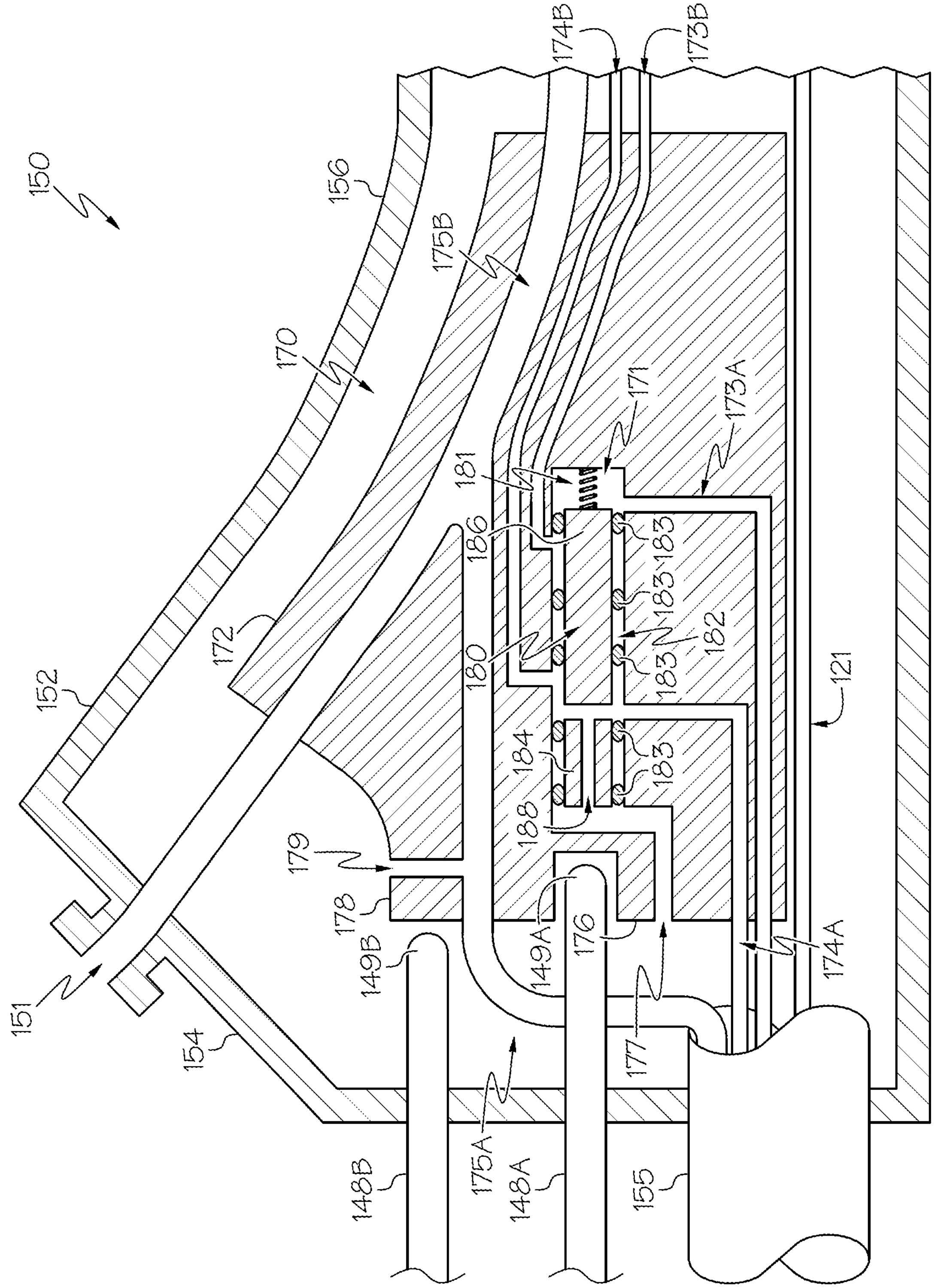
FIG. 12A is a partial cross-sectional view of the disposable body of the medical device of FIG. 1 including a valve manifold in a default configuration, according to aspects of this disclosure.
Figure 12B:
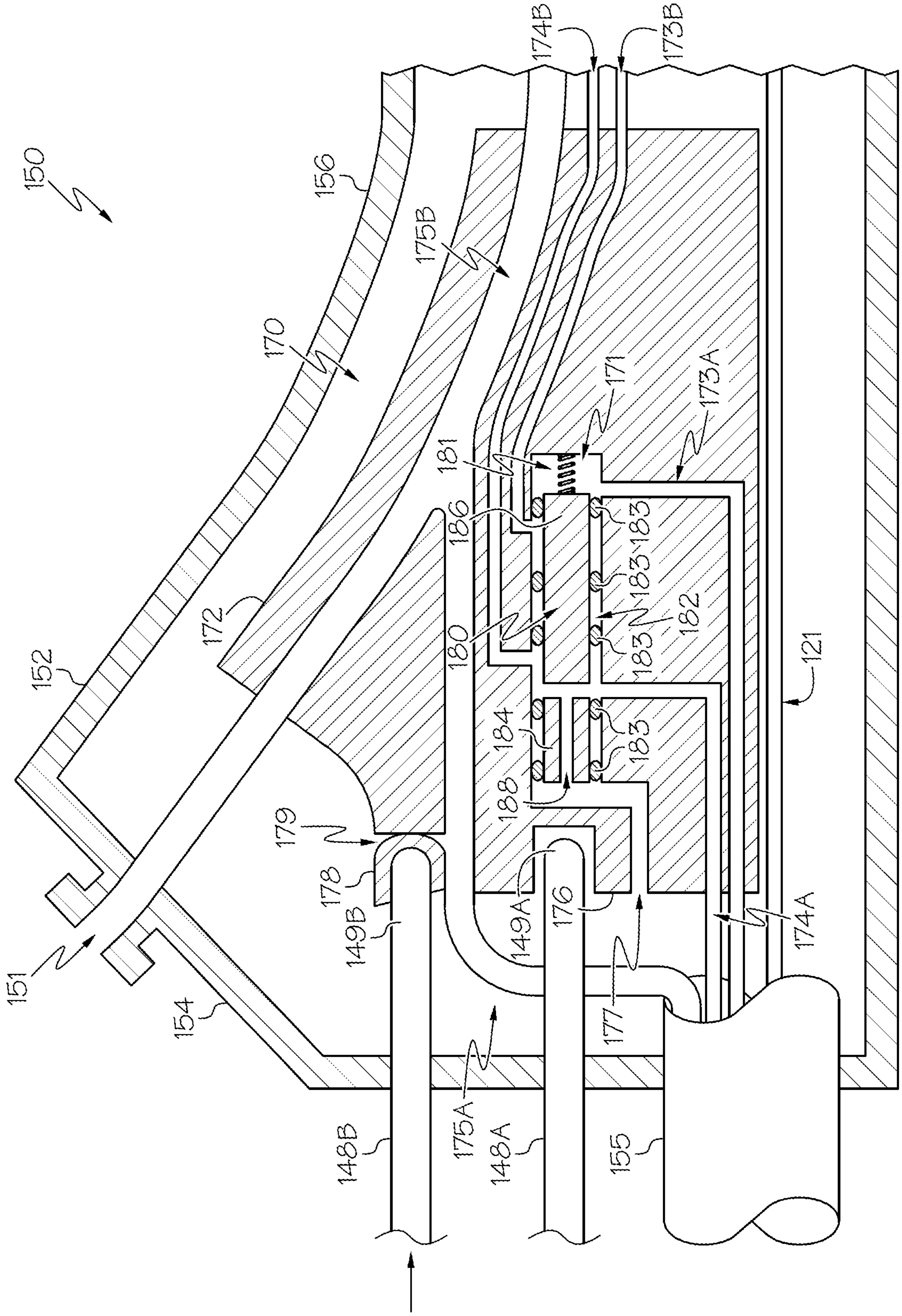
FIG. 12B is a partial cross-sectional view of the disposable body of the medical device of FIG. 1 with the valve manifold at least partially deformed, according to aspects of this disclosure.
Figure 12C:
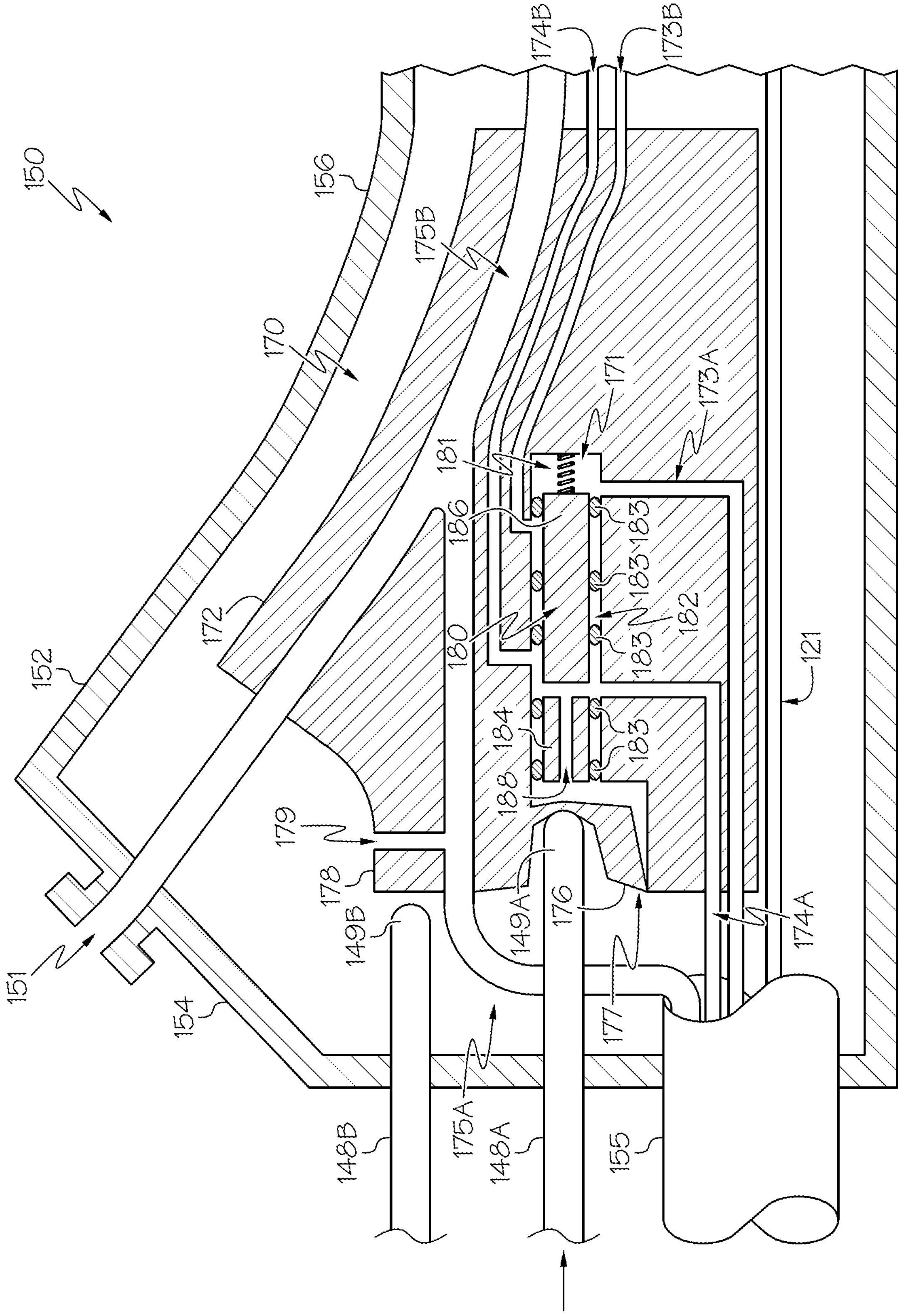
FIG. 12C is a partial cross-sectional view of the disposable body of the medical device of FIG. 1 with the valve manifold at least partially deformed, according to aspects of this disclosure.

Referring now to FIGS. 12A-12C, housing 152 of second body 150 is depicted with valve manifold 170 positioned proximate to proximal end 154. Valve manifold 170 may include a flexible body 172 including a proximal end and a distal end that is opposite the proximal end. Flexible body 172 may be formed of various elastic materials capable of moving, flexing, and/or at least partially deforming in response to an application of force thereto, such as, for example, by one or more components of first body 110 (e.g., movable rods). In some embodiments, flexible body 172 may be formed of an elastic membrane, rubber, and/or various other flexible materials capable of selective deformation. As described in detail herein, the proximal end of flexible body 172 may be configured and operable to interact with one or more components of first body 110 (e.g., the plurality of movable rods), such as at a first region 176, a second region 178, and more.

Valve manifold 170 may include a plurality of fluidics channels extending through flexible body 172, such as between the proximal end and the distal end. The plurality of fluidics channels may extend from fluidics tube assembly 155 and be received in valve manifold 170, thereby providing fluid communication between external device 10 and shaft 158. In some embodiments, the fluidics channels in valve manifold 170 may be integral with the fluidics channels within fluidics tube assembly 155, while in other embodiments valve manifold 170 and fluidics tube assembly 155 may include corresponding fluidics channels that are coupled to one another within housing 152.

Still referring to FIG. 12A, valve manifold 170 may further include a cavity 171 disposed within flexible body 172, and one or more of the plurality of fluidics channels may extend into cavity 171. Accordingly, one or more of the plurality of fluidics channels in valve manifold 170 may be in fluid communication with cavity 171. In the example, a first fluidics channel of valve manifold 170 may be segmented into a first segment 173A and a second segment 173B by cavity 171. In other words, cavity 171 may be disposed inline along the first fluidics channel such that the first fluidics channel may be separated into a pair of segments 173A, 173B.

Further, cavity 171 may be disposed inline along a second fluidics channel of valve manifold 170 such that the second fluidics channel may be segmented into a first segment 174A and a second segment 174B. A third fluidics channel of valve manifold 170 may be segmented into a first segment 175A and a second segment 175B, with first segment 175A extending into flexible body 172 from fluidics tube assembly 155 and second segment 175B extending into flexible body 172 from port 151. It should be understood that each of the second segments of the fluidics channels extend through distal end 156 and a longitudinal length of shaft 158, terminating at an opening located at distal tip 159 (FIG. 1).

In the example, the first fluidics channel (i.e. first segment 173A and second segment 173B) may define a water channel, the second fluidics channel (i.e. first segment 174A and second segment 174B) may define a pressurized air channel, and the third fluidics channel (i.e. first segment 175A and second segment 175B) may define a suction and working channel. It should be appreciated that additional and/or fewer channels may be included in valve manifold 170 and/or fluidics tube assembly 155 without departing from a scope of this disclosure. In some embodiments, fluidics tube assembly 155 may include one or more fluidics channels that are not coupled to valve manifold 170, such as, for example, a fourth fluidics channel 121. In this instance, fourth fluidics channel 121 may extend through housing 152 and into shaft 158, terminating at distal tip 159. In the example, fourth fluidics channel 121 may include a pressurized-water channel.

Still referring to FIGS. 12A-12C, valve manifold 170 may further include a movable valve 180 disposed within cavity 171. Movable valve 180 may include a movable valve body 182 (hereinafter "body 182") having a longitudinal length defined between a proximal end 184 and a distal end 186. In the embodiment, body 182 may have a cylindrical shape corresponding to a cross-sectional profile of cavity 171. Movable valve 180 may further include an internal lumen 188 disposed through body 182, such as at proximal end 184. Internal lumen 188 may be sized, shaped, and configured to extend between one or more sides of body 182, thereby facilitating fluid communication between the one or more sides of body 182.

In the embodiment, internal lumen 188 may define a T-shaped channel extending through body 182 and terminating at three openings along three different sides of body 182 (e.g., a first sidewall, a second sidewall, and proximal end 184). Accordingly, internal lumen 188 may facilitate fluid communication between the at least three sides of body 182. In other embodiments, internal lumen 188 may include various other suitable sizes, shapes, and/or configurations than those shown and described herein without departing from a scope of this disclosure. Movable valve 180 may further include one or more seals 183 (e.g., gaskets, O-rings, etc.) coupled to and disposed about an exterior of body 182.

The one or more seals 183 may be configured to form an air-tight fluid seal against an inner wall of flexible body 172 defining cavity 171.

Still referring to FIGS. 12A-12C, the one or more seals 183 may facilitate movement of movable valve 180 relative to cavity 171 by slidably engaging the inner wall of flexible body 172. In the example, movable valve 180 may include a first pair of seals 183 adjacent to proximal end 184, and a second pair of seals 183 adjacent to distal end 186. The first pair of seals 183 may be separated from one another on each side of body 182 by an opening of internal lumen 188. As described in further detail below, movable valve 180 may be configured to move within cavity 171, and relative to flexible body 172, to selectively adjust the fluid communication between the plurality of fluidics channels within valve manifold 170.

Valve manifold 170 may further include a biasing mechanism 181 (e.g., a spring) disposed within cavity 171. Biasing mechanism 181 may include a distal end and a proximal end, with the proximal end coupled to movable valve 180 at distal end 186. The distal end of biasing mechanism 181 may be coupled to an interior wall of flexible body 172 defining cavity 171, such that biasing mechanism 181 may be disposed between movable valve 180 and the interior wall defining cavity 171. Biasing mechanism 181 may be configured to apply a proximally-directed force against distal end 186, thereby urging movable valve 180 in a proximal direction when biasing mechanism 181 is in an expanded configuration (FIG. 12A). As described further herein, biasing mechanism 181 may be moved to a compressed configuration (FIG. 12C) in response to movable valve 180 moving distally relative to cavity 171.

Still referring to FIGS. 12A-12C, valve manifold 170 may include one or more vents forming an opening in flexible body 172, with the openings being in fluid communication with one or more of the plurality of fluidics channels. The one or more vents may connect the one or more fluidics channels with an atmospheric pressure from an internal cavity of housing 152. In the example, valve manifold 170 may include at least a first vent 177 and a second vent 179 positioned along the proximal end of flexible body 172. First vent 177 may be positioned adjacent to first region 176 along the proximal end of flexible body 172, and second vent 179 may be positioned adjacent to second region 178 along the proximal end of flexible body 172. As described further herein, first body 110 may be configured to selectively open and close first vent 177 and second vent 179 by moving first region 176 and second region 178, respectively, to control fluid communication between the fluidics channels of valve manifold 170.

According to an exemplary method of using medical device 100, first body (reusable handle) 110 may be coupled to second body (disposable tube) 150 (FIG. 1) in response to receiving distal end 116 within proximal end 154 (FIG. 4). Umbilicus assembly 120 may be coupled to first body 110 via a corresponding port along housing 112. In other embodiments, first body 110 and umbilicus assembly 120 may be a unitary component such that housing 112 and umbilicus tube 122 may be fixedly secured to one another.

Fluidics tube assembly 155 may extend through internal channel 111 (FIG. 2) and exit first body 110 at a corresponding port on housing 112. Fluidics tube assembly 155 may be fluidly coupled to external device 10 at distal end 157 to provide fluid communication between second body 150 and external device 10 through first body 110 (FIG. 1). As described in detail above, fluidics tube assembly 155 may shield first body 110 and umbilicus assembly 120 from fluid communication second body 150, and particularly the fluidics channels receiving and/or delivering various fluids and biological matter during the procedure.

Housing 112 may be locked to housing 152 via the receipt of depressible pin 113 into aperture 153 (FIGS. 5A-5C). It should be appreciated that the locking mechanism of medical device 100 (e.g. depressible pin 113 and aperture 153) may inhibit disengagement of first body 110 from second body 150 during use of medical device 100 during a procedure. First connector assembly 130 may engage second connector assembly 160 in response to proximal end 154 receiving distal end 116 and first body 110 rotating relative to second body 150 (or vice versa) when medical device 100 is assembled (FIGS. 9A-10B).

With first connector assembly 130 coupled to second connector assembly 160 (via an engagement of grasper tools 138 and pins 164), a user of medical device 100 may actuate the one or more control knobs 115 on first body 110 to control an articulation of shaft 158 and distal tip 159 on second body 150 (FIG. 1). As described above, each control knob 115 may be coupled to at least one gear 133, and each gear 133 may be further coupled to at least a pair of movable rods 132 along gear racks 135 (FIG. 6). Accordingly, rotation of control knobs 115 may provide for a translation of movable rods 132 relative to housing 112 and a corresponding translation of wires 168 relative to housing 152. With a distal end of each wire 168 coupled to an interior surface of shaft 158, control knobs 115 may control an articulation (e.g., lateral and vertical deflection) of shaft 158 and distal tip 159.

Further, the plurality of movable rods may extend into second body 150 to control actuation of one or more components of second body 150, such as fluid communication between the fluidics channels of valve manifold 170. As described above, each of second actuator 118 and third actuator 119 may be movably coupled to a corresponding movable rod 148A, 148B via a coupling mechanism 140A, 140B (FIG. 11). Actuation of second actuator 118 and/or third actuator 119 may provide for a translation of movable rods 148A, 148B relative to housing 112 and housing 152. With distal ends 149A, 149B received within housing 152 and positioned adjacent to valve manifold 170, second actuator 118 and third actuator 119 may control an operation of valve manifold 170.

Referring specifically to FIG. 12A, valve manifold 170 is depicted in an unactuated state with first movable rod 148A and second movable rod 148B separated from the proximal end of flexible body 172. A position of first movable rod 148A and second movable rod 148B corresponds to an unactuated state of second actuator 118 and third actuator 119, respectively. In this instance, movable valve 180 may remain in a first (proximal) position with biasing mechanism 181 in an expanded (default) configuration. It should be appreciated that the first (proximal) position may define a default position of movable valve 180. Further, the proximal end of flexible body 172, and particularly first region 176 and second region 178, remain in a first (unactuated) position. Accordingly, first vent 177 and second vent 179 may be maintained in an open state.

In this instance, a fluid (e.g., water) received within first segment 173A of the first fluidics channel may be maintained within valve manifold 170 while movable valve 180 is positioned in the first (proximal) position. For example, the fluid received into cavity 171 via first segment 173 may be inhibited from extending into second segment 173B due to a relative position of the plurality of seals 183, and particularly a distalmost seal 183 on distal end 186. Accordingly, the distalmost seal 183 may be positioned between an outlet of first segment 173A into cavity 171 and an inlet of second segment 173B from cavity 171, thereby sealing the fluid from first segment 173A within cavity 171.

Still referring to FIG. 12A, with movable valve 180 in the first (proximal) position, a fluid (e.g., pressurized air) received within first segment 174A of the second fluidics channel may be received in cavity 171 and internal lumen 188, which is aligned with the outlet of first segment 174A into cavity 171. As first movable rod 148A is separated from the proximal end of flexible body 172, and particularly first region 176, first vent 177 may be maintained in an open configuration. Accordingly, the fluid received in internal lumen 188 may be directed toward first vent 177, which provides access to an internal atmosphere of housing 152. In some embodiments, the fluid (e.g. pressurized air) received within the cavity of housing 152 may be released from second body 150, such as via one or more openings (not shown) on housing 152.

It should be appreciated that movable valve 180 may facilitate access to both second segment 174B and first vent 177 via internal lumen 188 when in the first (proximal) position. Valve manifold 170 may be configured such that the fluid (e.g., pressurized air) received from first segment 174A may be directed toward first vent 177 (e.g., atmospheric pressure) in lieu of second segment 174B as a path of least resistance.

First segment 175A of the third fluidics channel may be fluidly coupled to a negative pressure source such that a negative pressure may be generated through valve manifold 170 via first segment 175A. With second movable rod 148B separated from the proximal end of flexible body 172, and particularly second region 178, second vent 179 may be maintained in an open configuration. Accordingly, any negative pressure received in first segment 175A may be directed toward second vent 179, which provides access to an internal atmosphere of housing 152.

Referring now to FIG. 12B, valve manifold 170 is depicted in a first actuated state with second movable rod 148B translated distally and abutting against the proximal end of flexible body 172, corresponding to an actuated state of third actuator 119. In some embodiments, medical device 100 may be configured to generate a feedback (e.g., audible, tactile, etc.) in response to valve manifold 170 transitioning to the first actuated state, such as in response to second movable rod 148B interfacing with flexible body 172.

The proximal end of flexible body 172, and particularly second region 178, may move to a second (actuated) position in response to second movable rod 148B applying a distally-directed force thereto. In this instance, flexible body 172 at second region 178 may be at least partially deformed in response to the distal translation of distal end 149B, thereby causing second vent 179 to move from the open configuration (FIG. 12A) to a closed configuration. With second vent 179 closed, the fluid (e.g., negative pressure) generated in first segment 175A may travel through second segment 175B. It should be understood that second segment 175B may extend through shaft 158 and terminate at distal tip 159 (FIG. 1), such that suction may be provided at distal tip 159 during the procedure. Accordingly, third actuator 119 may be configured to control fluid communication through the third fluidics channel of valve manifold 170.

Referring now to FIG. 12C, valve manifold 170 is depicted in a second actuated state with first movable rod 148A translated distally and abutting against the proximal end of flexible body 172, corresponding to an actuated state of second actuator 118. In this instance, second movable rod 148B may be returned to a proximal position such that distal end 149B no longer abuts against flexible body 172. In some embodiments, medical device 100 may be configured to generate a feedback (e.g., audible, tactile, etc.) in response to valve manifold 170 transitioning to the second actuated state, such as in response to first movable rod 148A interfacing with flexible body 172. In this instance, movable valve 180 remains in the first (proximal) position with biasing mechanism 181 in the expanded (default) configuration.

The proximal end of flexible body 172, and particularly first region 176, may move to a second (actuated) position in response to first movable rod 148A applying a distally-directed force thereto. In this instance, flexible body 172 at first region 176 may be at least partially deformed in response to the distal translation of distal end 149A, thereby causing first vent 177 to move from the open configuration (FIG. 12A) to a closed configuration. With first vent 177 closed and movable valve 180 maintained in the first (proximal) position relative to cavity 171, the fluid (e.g., pressurized air) received from first segment 174A may travel through internal lumen 188 and into second segment 174B.

It should be understood that second segment 174B may extend through shaft 158 and terminate at distal tip 159 (FIG. 1), such that the fluid may be delivered from distal tip 159 to provide insufflation during the procedure. Accordingly, second actuator 118 may be configured to control fluid communication through the second fluidics channel of valve manifold 170. With movable valve 180 maintained in the first (proximal) position and biasing mechanism 181 in the expanded (default) configuration, fluid (e.g., water) received in valve manifold 170 from first segment 173A of the first fluidics channel remains within cavity 171 and sealed from accessing second segment 1736 by the one or more seals 183.

Figure 12D:
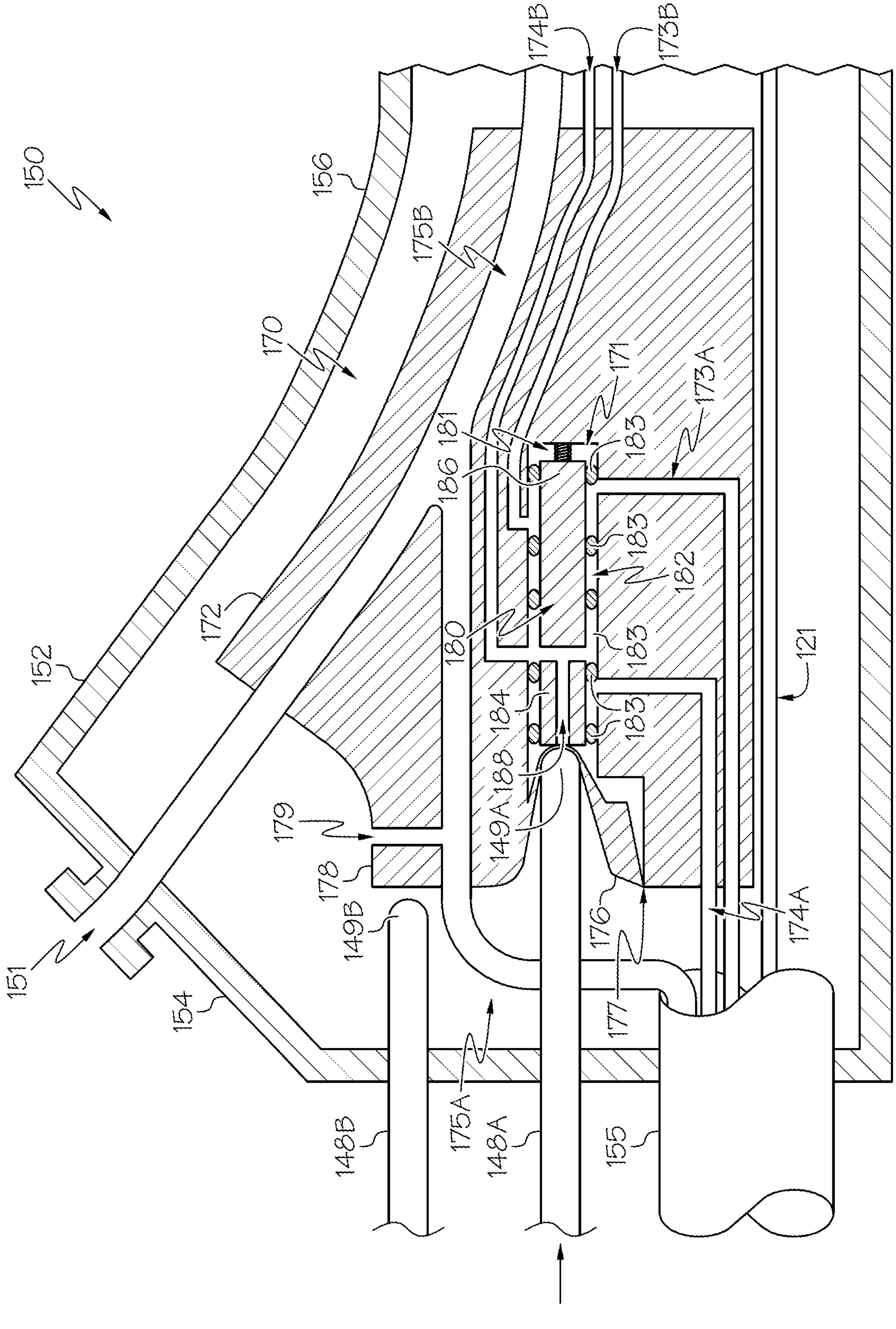
FIG. 12D is a partial cross-sectional view of the disposable body of the medical device of FIG. 1 with the valve manifold at least partially deformed, according to aspects of this disclosure.

Referring now to FIG. 12D, valve manifold 170 is depicted in a second actuated state with first movable rod 148A translated further distally and abutting against the proximal end of flexible body 172, corresponding to a second actuated state of second actuator 118. In some embodiments, medical device 100 may be configured to generate a feedback (e.g., audible, tactile, etc.) in response to valve manifold 170 transitioning to the third actuated state, such as in response to distal end 149A interfacing with flexible body 172. In this instance, movable valve 180 is moved (e.g., translated) to a second (distal) position with biasing mechanism 181 in a compressed configuration within cavity 171. It should be appreciated that the second (distal) position defines an actuated position of movable valve 180.

The proximal end of flexible body 172, and particularly first region 176, is moved to a third (actuated) position in response to distal end 149A applying a distally-directed force thereto. It should be appreciated that the force applied is relatively greater than the force applied by distal end 149A in FIG. 12B. In this instance, flexible body 172 may be at least partially deformed, thereby abutting against proximal end 184 and causing movable valve 180 to translate relative to cavity 171. In this instance, fluid communication between first segment 174A and second segment 174B of the second fluidics channel is no longer provided through internal lumen 188 given a relocation of movable valve 180, such that the fluid (e.g., pressurized air) received through valve manifold 170 via the second fluidics channel is terminated.

Additionally, with distal end 186 moved distally relative to cavity 171, the one or more seals 183 may move to establish fluid communication between first segment 173A and second segment 173B of the first fluidics channel. In this instance, the one or more seals 183 are moved and no longer inhibit the fluid (e.g. water) received into cavity 171 from first segment 173A from being blocked for receipt in second segment 173B. It should be understood that second segment 173B may extend through shaft 158 and terminate at distal tip 159 (FIG. 1), such that the fluid may be delivered from distal tip 159 to provide irrigation during the procedure. Accordingly, second actuator 118 may be configured to control fluid communication through the first fluidics channel of valve manifold 170.

Actuation of first actuator 117 may provide for a translation of at least one movable rod 132 relative to housing 112 and a corresponding translation of at least one wire 168 relative to housing 152 (via a connection between first connector assembly 130 and second connector assembly 160), thereby causing actuation of a device (e.g., an elevator) at distal tip 159.

Upon completion of the procedure with medical device 100, a user may disassemble first body 110 from second body 150 by actuating depressible pin 113 and rotating first body 110 relative to second body 150 (or vice versa). As first body 110 is rotated relative to second body 150, first connector assembly 130 may disengage second connector assembly 160. With depressible pin 113 removed from aperture 153, first body 110 may be pulled proximally to retract distal end 116 from within proximal end 154. With second body 150 decoupled from first body 110 and fluidics tube assembly 155 retracted from internal channel 111, second body 150 may be disposed of by a user of medical device 100. First body 110 and/or umbilicus assembly 120 may be reprocessed and cleaned for further use given that the plurality of fluidics channels containing biological matters (e.g., biohazardous fluids) were contained within second body 150.

Each of the aforementioned systems, devices, assemblies, and methods may be used to treat a target treatment site with a modular medical device capable of selective assembly and disassembly. By providing a medical device with reusable and disposable components capable of establishing mechanical, electrical, and fluidic connection with one another, instances of material waste from fully disposable devices, and cross-contamination between patients through use of fully reusable devices, may be minimized.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:

a first body including:

a first actuation member including a first connector; and a second actuation member;

a second body for attachment to, and detachment from, the first body, the second body including:

an actuation wire;

a second connector at a proximal end of the actuation wire; and a valve having one or more channels for receiving a material;

wherein attachment of the first body with the second body results in the first connector engaging the second connector, such that movement of the first actuation member causes a corresponding movement of the actuation wire; and wherein moving the second actuation member into the second body to interact with the valve is configured to selectively direct the material through the one or more channels.

2. The medical device of claim 1, wherein the second actuation member is configured to close an opening of at least one of the one or more of channels by at least partially deforming the valve at the opening.

3. The medical device of claim 1, wherein the second body includes a movable valve body disposed within the valve, the movable valve body being biased to a first position by a biasing mechanism positioned against the movable valve body.

4. The medical device of claim 3, wherein the second actuation member is configured to compress the biasing mechanism and move the movable valve to a second position.

5. The medical device of claim 1, wherein the first body includes a channel and the second body includes a fluidics tube configured to receive the material from a source, wherein the channel is configured to receive the fluidics tube through the first body.

6. The medical device of claim 1, wherein the first body includes an actuator coupled to the first actuation member, and the second body includes a shaft coupled to a distal end of the actuation wire.

7. The medical device of claim 6, wherein the actuator is configured to articulate the shaft in response to actuator moving the first actuation member, and the first actuation member moving the actuation wire, when the first connector is engaged with the second connector.

8. The medical device of claim 1, wherein the first connector includes a grasper, and the second connector includes a pair of pins defining a gap sized to receive the grasper between the pair of pins.

9. The medical device of claim 8, wherein the grasper is configured to engage the pair of pins by extending through the gap to couple the first actuation member to the actuation wire.

10. The medical device of claim 9, wherein the grasper is configured to extend through the gap in response to the first body rotating in a first direction relative to the second body when the first body is at least partially received within the second body.

11. The medical device of claim 10, wherein the grasper is configured to disengage the pair of pins from the grasper in response to the first body rotating in a second direction relative to the second body that is opposite of the first direction.

12. The medical device of claim 6, wherein the actuation wire is configured to move relative to the second body in response to the first actuation member moving relative to the first body.

13. The medical device of claim 1, wherein the first body includes an actuator coupled to a gear, and the first actuation member includes a gear rack configured to mesh with the gear.

14. The medical device of claim 13, wherein the actuator is configured to translate the first actuation member and the first connector by rotating the gear.

15. The medical device of claim 1, further including a locking mechanism having a pin on the first body, and an aperture on the second body that is configured to receive the pin when the first body is received within, and rotated relative to, the second body, thereby fixing an axial position of the first body relative to the second body.

16. A medical device, comprising:

a proximal handle including:

a handle housing including a channel;

an actuation rod disposed within and movable relative to the handle housing;

an actuator movably coupled to the actuation rod; and a shaft assembly including:

a shaft housing including a fluidics tube extending proximally from the shaft housing, the fluidics tube configured to extend through the channel of the handle housing;

a valve manifold disposed within the shaft housing; and at least one fluidics channel defined by the valve manifold and in fluid communication with the fluidics tube;

wherein the actuator is configured to control the fluid communication between the at least one fluidics channel and the fluidics tube by abutting the actuation rod against the valve manifold to at least partially deform the valve manifold.

17. The medical device of claim 16, wherein the valve manifold includes a movable valve body and a biasing mechanism disposed within the valve manifold, wherein the movable valve body is biased to a default position when the biasing mechanism is in an expanded configuration; and wherein the at least one fluidics channel is in fluid communication with the fluidics tube when the movable valve body is in the default position.

18. The medical device of claim 17, wherein the actuator is configured to move the movable valve body to an actuated position by urging the biasing mechanism to a compressed configuration;

wherein the at least one fluidics channel is not in fluid communication with the fluidics tube when the movable valve body is in the actuated position.

19. The medical device of claim 16, wherein the proximal handle includes a first connector and a second actuation rod coupled to the first connector, the first connector is movable relative to the handle housing in response to movement of the second actuation rod, and the shaft assembly includes a second connector and an actuation wire coupled to the second connector, the second connector is movable relative to the shaft housing in response to movement of the actuation wire; and wherein the second actuation rod is configured to move the actuation wire when the first connector is mated with the second connector.

20. A medical device, comprising:

a first body including:

an actuator;

a movable rod coupled to the actuator and configured to move in response to actuation of the actuator; and a second body selectively attachable to the first body, the second body including:

a valve having a flexible body; and a plurality of channels configured to deliver a material through the second body;

wherein the actuator is configured to selectively divert the material through the plurality of channels in response to moving the movable rod against the valve to at least partially deform the flexible body.

* * * * *